(12) United States Patent
Terazono et al.

(10) Patent No.: US 9,023,294 B2
(45) Date of Patent: May 5, 2015

(54) CELL ANALYZER

(75) Inventors: Hideyuki Terazono, Kawasaki (JP);
Kenji Yasuda, Tokyo (JP); Masahito Hayashi, Kawasaki (JP); Hiroyuki Takei, Kawasaki (JP); Akihiro Hattori, Tokyo (JP)

(73) Assignees: Kanagawa Academy of Science and Technology, Kanagawa (JP); National University Corporation Tokyo Medical and Dental University, Tokyo (JP); On-Chip Cellonics Consortium Co., Ltd., Tokyo (JP)

( * ) Notice: Subject to any disclaimer, the term of this patent is extended or adjusted under 35 U.S.C. 154(b) by 327 days.

(21) Appl. No.: 13/261,410

(22) PCT Filed: Feb. 24, 2011

(86) PCT No.: PCT/JP2011/054174
§ 371 (c)(1),
(2), (4) Date: Oct. 10, 2012

(87) PCT Pub. No.: WO2011/105507
PCT Pub. Date: Sep. 1, 2011

(65) Prior Publication Data
US 2013/0029407 A1    Jan. 31, 2013

(30) Foreign Application Priority Data
Feb. 24, 2010  (JP) .................................. 2010-038210

(51) Int. Cl.
*C12M 3/00*  (2006.01)
*C12M 1/00*  (2006.01)
(Continued)

(52) U.S. Cl.
CPC .. *G01N 1/31* (2013.01); *G01N 1/34* (2013.01); *C12N 1/066* (2013.01); *G01N 1/4077* (2013.01); *G01N 15/1459* (2013.01); *G01N 15/1463* (2013.01); *G01N 21/6408* (2013.01);
(Continued)

(58) Field of Classification Search
None
See application file for complete search history.

(56) References Cited

U.S. PATENT DOCUMENTS

2001/0036669 A1*  11/2001  Jedrzejewski et al. .......... 436/94
2006/0019379 A1*  1/2006  Taylor et al. ............... 435/306.1
(Continued)

FOREIGN PATENT DOCUMENTS

WO    WO 2004/050220 A1    6/2004
WO    WO 2006/106823 A1    10/2006
(Continued)

OTHER PUBLICATIONS

H.Ji, D.Sander, A.Haas, P.Abshire, "A CMOS Contact Imager for Locating Individual Cells," IEEE International Symposium on Circuits and Systems, 2006.*
(Continued)

*Primary Examiner* — Jill Warden
*Assistant Examiner* — Benjamin Whatley
(74) *Attorney, Agent, or Firm* — Foley & Lardner LLP

(57) ABSTRACT

Provided is a cell concentration and purification device, having: a function of continuously concentrating cells; a function of then subsequently disposing the cells continuously in a specific region of a channel; a function of simultaneously recognizing, based on an image, the shape and fluorescence emission of each single cell; and a function of recognizing the cells and then separating and purifying the same based on the data relating to the shape and fluorescence emission thereof.

8 Claims, 18 Drawing Sheets

(51) Int. Cl.
*G01N 1/31* (2006.01)
*C12N 1/06* (2006.01)
*G01N 1/40* (2006.01)
*G01N 15/14* (2006.01)
*G01N 21/64* (2006.01)
*G01N 1/34* (2006.01)

(52) U.S. Cl.
CPC .... *G01N21/6428* (2013.01); *G01N 2001/4094* (2013.01); *G01N 2015/149* (2013.01); *G01N 2021/6482* (2013.01)

(56) References Cited

U.S. PATENT DOCUMENTS

| | | | |
|---|---|---|---|
| 2006/0070951 | A1 | 4/2006 | Baba et al. |
| 2006/0246575 | A1* | 11/2006 | Lancaster et al. .......... 435/287.2 |
| 2006/0252054 | A1* | 11/2006 | Lin et al. ........................ 435/6 |
| 2007/0059763 | A1* | 3/2007 | Okano et al. .................. 435/7.1 |
| 2007/0183935 | A1* | 8/2007 | Clemmens et al. ........... 422/100 |
| 2007/0202536 | A1* | 8/2007 | Yamanishi et al. ............ 435/7.1 |
| 2009/0117005 | A1* | 5/2009 | Rousseau ........................ 422/64 |
| 2009/0130719 | A1* | 5/2009 | Handique .................... 435/91.2 |
| 2009/0232773 | A1 | 9/2009 | Kato et al. |
| 2011/0014646 | A1 | 1/2011 | Fukuda et al. |
| 2011/0014685 | A1 | 1/2011 | Fukuda et al. |
| 2012/0088295 | A1* | 4/2012 | Yasuda et al. ............. 435/288.7 |
| 2014/0242678 | A1* | 8/2014 | Boos et al. .................... 435/259 |

FOREIGN PATENT DOCUMENTS

| | | |
|---|---|---|
| WO | WO 2008/130977 A2 | 10/2008 |
| WO | WO 2009/021215 A1 | 2/2009 |
| WO | WO 2009/123000 A1 | 10/2009 |

OTHER PUBLICATIONS

Burns, R.D., Shah, J., Canaan Hong, Pepic, S., Ji Soo Lee, Homsey, R.I., Thomas, P., "Object location and centroiding techniques with CMOS active pixel sensors," Electron Devices, IEEE Transactions on Electron Devices, vol. 50, No. 12, pp. 2369-2377, Dec. 2003. doi: 10.1109/TED.2003.819260.*

Takahashi K, Hattori A, Suzuki I, Ichiki T, Yasuda K. "Non-destructive on-chip cell sorting system with real-time microscopic image processing". J Nanobiotechnology vol. 2, issue 5, 2004.*

Fiedler et al., "Dielectrophoretic Sorting of Particles and Cells in a Microsystem," Anal. Chem., 1998, 70:1909-1915.

Hoffmann et al., "A new approach for analyzing cellular infiltration during allergic airway inflammation," Journal of Immunological Methods, 2007, 328:21-33.

Kamarck, Michael E., "Fluorescence-Activated Cell Sorting of Hybrid and Transfected Cells," Methods in Enzymology, 1987, 151:150-165.

Wolff et al., "Rare event cell sorging in a microfluidic system for application in prenatal diagnosis," Micro Total Anal. Syst., 1998, 98:77-80.

* cited by examiner

Fig. 4
A
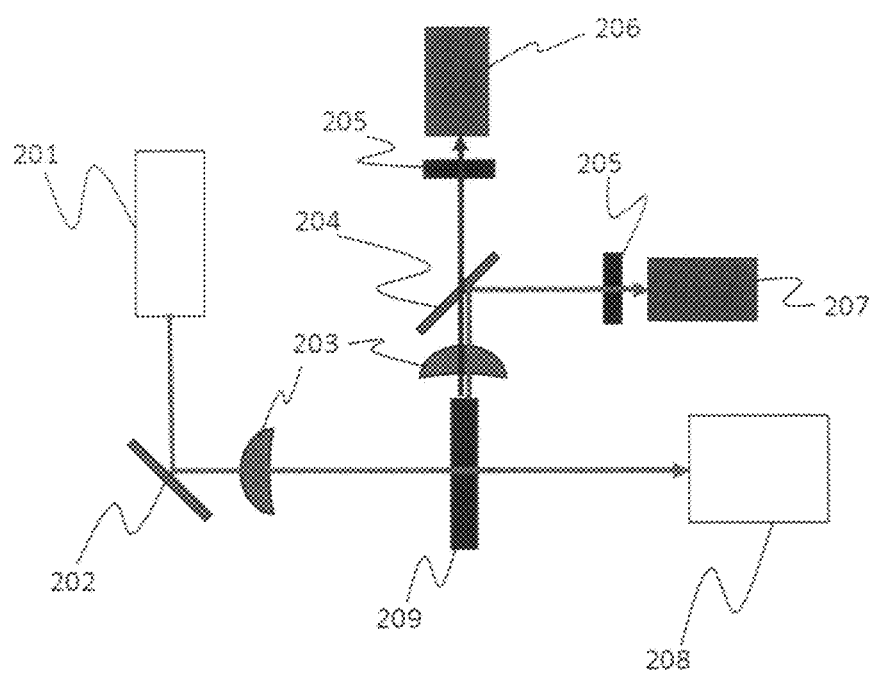
B
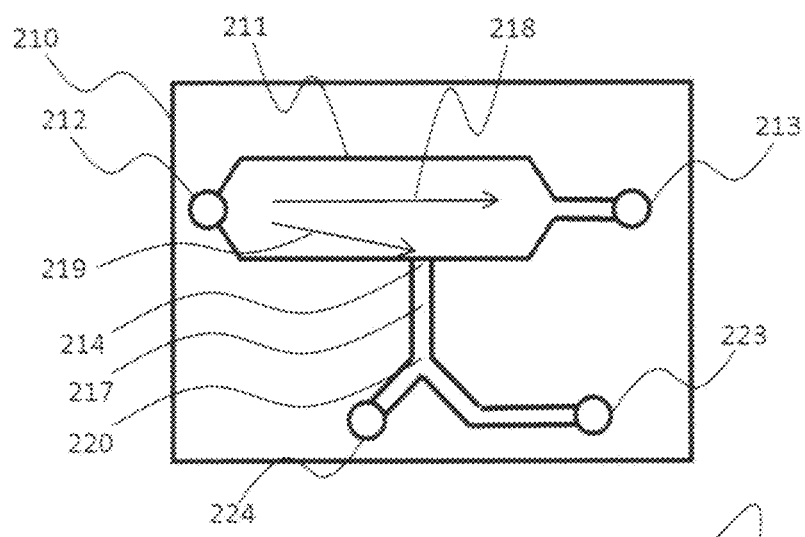
C
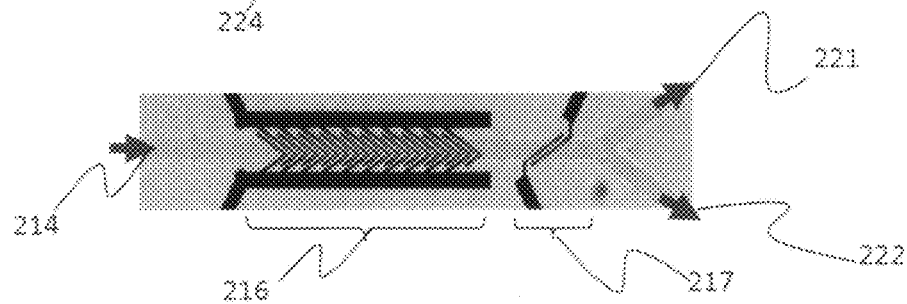

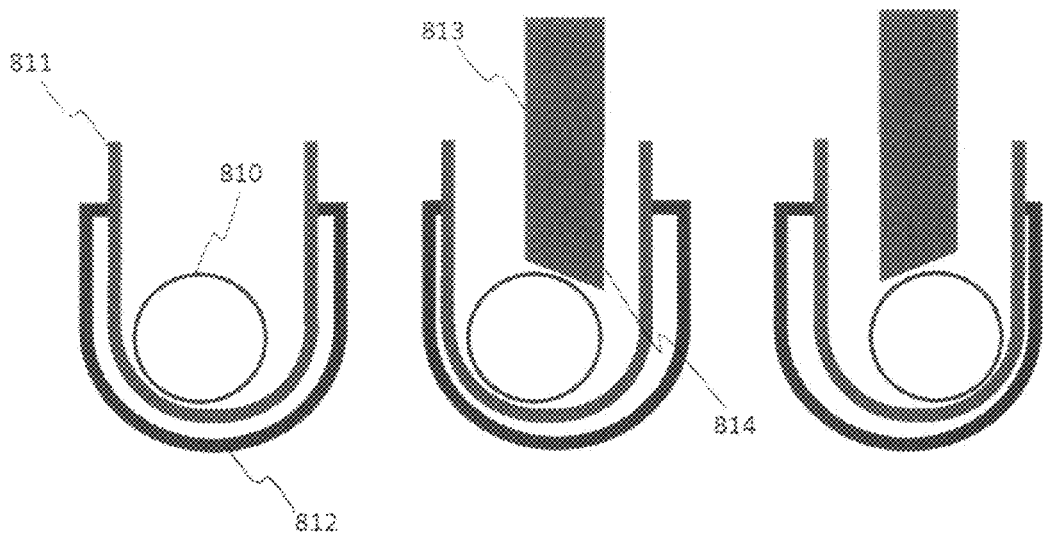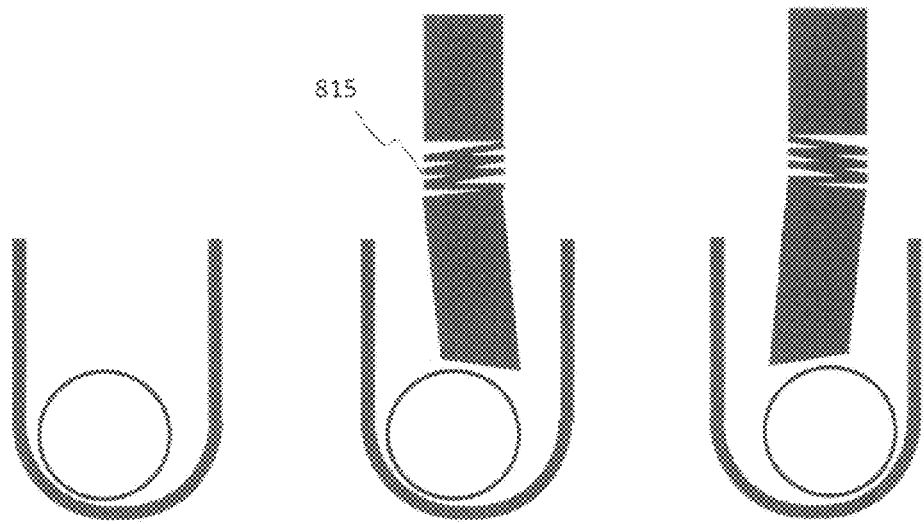

Fig. 17
A. State of cell
(a) Cytostatic state (with nucleus)  (b) Cell division state (no nucleus)
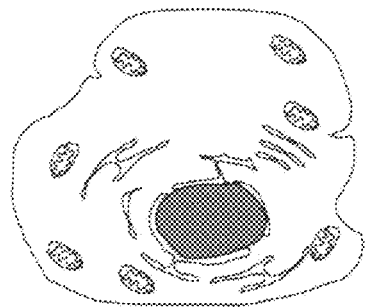 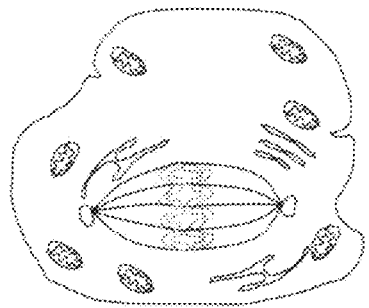
B. Camera image (schematic view)
(a) Cytostatic state (with nucleus)  (b) Cell division state (no nucleus)
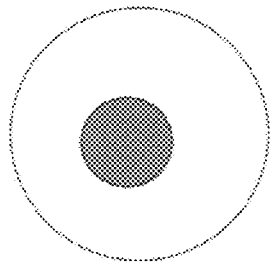 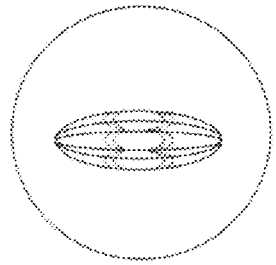

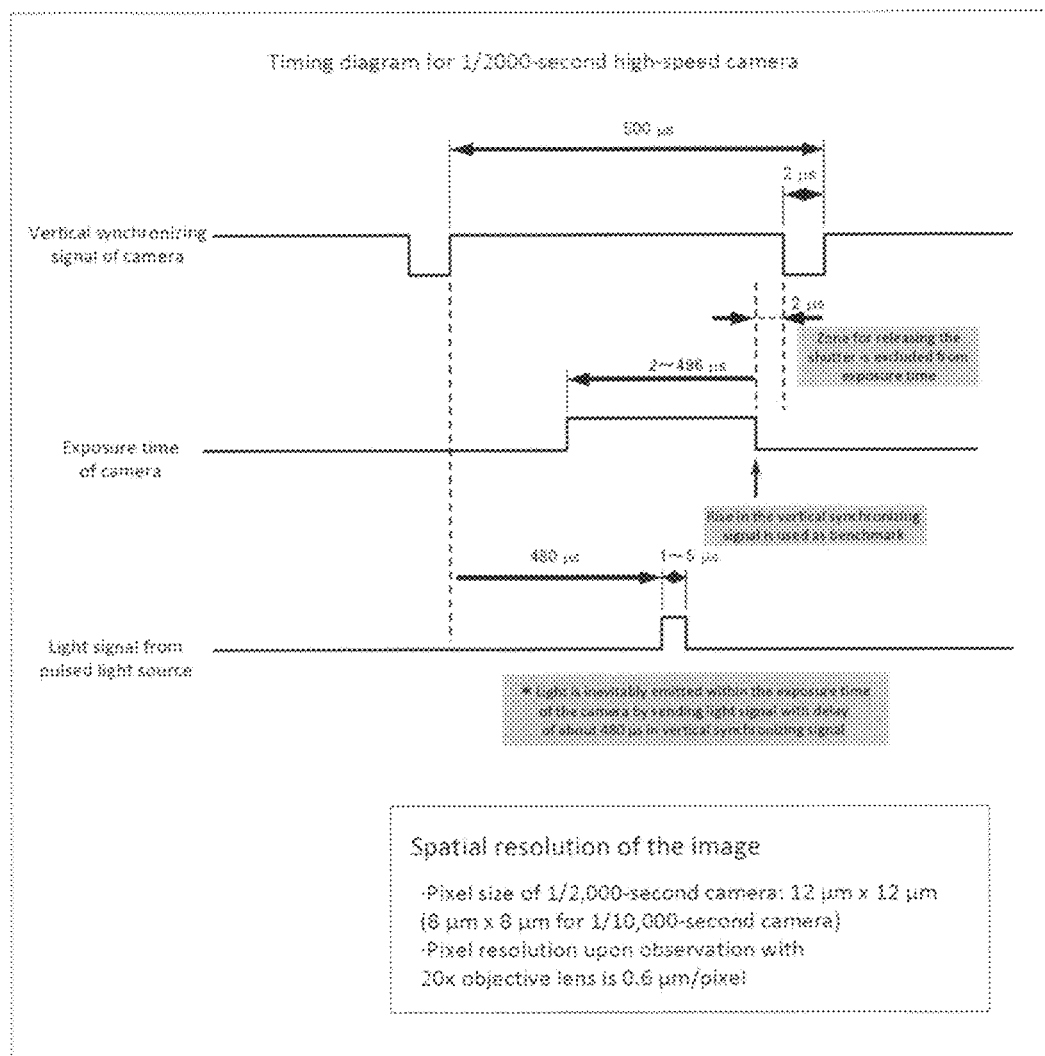

CELL ANALYZER

CROSS-REFERENCE TO RELATED APPLICATIONS

This application is a National Stage application of PCT/JP2011/054174, filed Feb. 24, 2011, which claims priority from Japanese application JP 2010-038210, filed Feb. 24, 2010.

TECHNICAL FIELD

The present invention relates to a cell analyzer.

BACKGROUND ART

In biological tissues of a multicellular organism, various cells play their own roles and maintain harmonious functions as a whole. Alternatively, a part of the cells turn into cancer (herein, "cancer" and "tumor" are collectively referred to as "cancer"), then it becomes a neoplasm that is different from the surrounding region. There is not necessarily a clear-cut boundary between the cancerous region and a normal tissue region which is remote from the cancerous region, and the regions surrounding the cancerous region are also affected to some extent. Therefore, in order to analyze a function of cells in an organ tissue, it is necessary to separate and analyze a small number of cells present in a small region as simple as possible in a short period of time and with minimum loss.

In addition, in the field of regenerative medicine, organ stem cells are separated from a tissue and recultivated to induce differentiation in an attempt to regenerate the tissue of interest and eventually to regenerate the organ.

Cells need to be distinguished according to some sort of indicators in order to identify or separate the cell. In general, the following methods are used to distinguish cells.
1) Morphological cell sorting by visual observation: Examples include screening of bladder cancer or unitary tract cancer by assessing atypical cells that appear in the urine, as well as screening of cancers by sorting atypical cells in blood or cytologically diagnosing the tissue.
2) Cell sorting by cell-surface antigen (marker) staining according to a fluorescence-antibody technique: A cell surface antigen, which is generally called a CD marker, is stained with a fluorescence-labeled antibody specific thereto. It is utilized for cell separation with a cell sorter, cancer screening using a flow cytometer or tissue staining, and the like. Indeed, they are not only used for medical care but also frequently used in physiological studies of cells and industrial application of cells.
3) Alternatively, for separation of the stem cells, there is an example in which cells including stem cells are roughly separated using a fluorescent dye that is incorporated into the cells as a reporter, and subsequently stem cells of interest are separated by performing cultivation. In this case, since no effective marker of the stem cells has been established, the cells of interest are separated through cultivation using only those showing induction of differentiation.

It is an important technique for biological and medical analyses to separate and collect a particular cell(s) from a culture solution. When cells are to be separated based on the difference in the specific weight of the cells, they can be separated by velocity sedimentation. However, when there is little difference in their specific weights, such as when naive cells and sensitized cells are to be distinguished, cells need to be separated one by one based on information obtained from fluorescence-antibody staining or visual observation.

When it comes to such technique, there has been a cell sorter, for example. A cell sorter is the technique in which fluorescence-stained cells are isolated into an electrically-charged droplet on single-cell bases and allowed to fall as a drop. A high electrical field is applied in an arbitrary direction along the normal plane with respect to the falling direction of the drop while the drop is falling so as to control the destination of the falling drops based on the presence or absence of the fluorescence of the cells in the droplet and the magnitude of light scattering so as to fractionate the drops into multiple containers beneath and collect them (Non-patent Document 1: Kamarck, M. E., Methods Enzymol. Vol. 151, p 150-155 (1987)).

However, there are problems with this technique such as that it is expensive, the size of the apparatus is large, an electrical field as high as a few thousand volts is required, a large amount of sample that has been concentrated to a certain degree is required, the cells may be damaged during generation of the droplets, and the sample cannot directly be observed. In order to solve these problems, a cell sorter has recently been developed for which a micro manufacturing technique is used to prepare a fine channel so that cells that flow through a laminar flow in the channel can directly be observed with a microscope for separation (Non-patent Document 2: Micro Total Analysis, 98, pp. 77-80 (Kluwer Academic Publishers, 1998); Non-patent Document 3: Analytical Chemistry, 70, pp. 1909-1915 (1998)). In a cell sorter produced by this micro manufacturing technique, however, the response speed for the separation of the sample is slow with respect to observation means. Thus, a need exists for a separation method that gives faster response and no damage to the sample. In addition, there are problems that the concentration of the cells in the sample solution under use has to be increased to a certain degree in advance or otherwise a subtle cell concentration prevents the separation efficiency of the device from being sufficiently enhanced; and further that when a small amount of sample is to be concentrated in a different apparatus, it is not only difficult to collect the concentrated solution without loss but also the cells might be contaminated during this cumbersome pretreatment stage, which are unfavorable in regenerative medicine and the like.

In order to solve these problems, the present inventors have utilized a micro manufacturing technique in developing a device for analyzing and separating a cell, which can be used to fractionate the sample based on the microconfiguration of the sample and the fluorescence distribution in the sample, and easily analyze and separate the cell sample without giving damage to the collected sample (Patent Document 1: Japanese Patent Unexamined Application Publication No. 2003-107099; Patent Document 2: Japanese Patent Unexamined Application Publication No. 2004-85323; Patent Document 3: WO2004/101731). This cell sorter is sufficiently practical in a laboratory level, but when it comes to general use in regenerative medicine, new techniques need to be developed for liquid transport process, collection process and pretreatments such as preparation of the sample.

Currently, although detection of cancerous tissues has been tremendously improved owing to the improvement in MRI (magnetic resonance imaging) and CT (computed tomography), no technique that is superior to the assessment method by biopsy for identifying benign and malignant tumors is present. There is one issue known for malignant tumors that the cancer cells metastasize from their tissues to other organs due to their ability to invade the blood vessels or the lymph vessels. Such malignant tumor cells that circulate in the peripheral blood are called peripheral blood-circulating cancer cells (Circulating Tumor Cells: CTCs), where approximately a few hundreds of cancer cells are thought to be present in one hundred thousand blood cells (including erythrocytes). Recently, carcinostatic agents for particular targets are being developed one after another, and it has become possible to select a carcinostatic drug that effectively disrupts the cell if the type of the malignant tumor in the blood is identified. If technique of monitoring CTCs flowing in the blood has been realized, the presence of malignant tumor cells causing the metastatic cancer flowing in the blood can quantitatively be measured. Then continuous and quantitative assessment of the effect of the administered carcinostatic drug will be possible, which will then lead to realization of the world's first technique that not only prevents administration of unnecessary carcinostatic drugs or administration of excessive amount of the carcinostatic drug, but also detects the presence or absence of recurrence.

With respect to genetic diagnosis and expression analysis, polymerase chain reaction (hereinafter, simply referred to as PCR) is a method for amplifying a particular nucleotide sequence from a mixture of various types of nucleic acids. Using PCR, a particular nucleic acid sequence can be amplified by adding a DNA template such as genomic DNA or complementary DNA that has been reverse-transcribed from messenger RNA, two or more types of primers, a thermostable enzyme, salt such as magnesium, and four types of deoxyribonucleoside triphosphates (dATP, dCTP, dGTP, dTTP) to a mixture of various types of nucleic acids, and then repeating the following steps at least one cycle: a step of separating the nucleic acids into single strands; a step of binding the primers with the separated nucleic acids; and a step of using the primer-bound nucleic acids as a template for hybridization using the thermostable enzyme. According to PCR, a thermal cycle is utilized in which the temperature of a reaction container used for the DNA amplification reaction is increased and decreased. Various mechanisms are used for changing the temperature. Examples include: a mechanism in which the temperature of a reaction container containing a sample is changed by heat exchange using a heater, a Peltier device or hot air; a mechanism in which the temperature is changed by alternately bringing a reaction container into contact with block heaters and liquid vessels at different temperatures; and a mechanism in which the temperature is changed by running a sample in a channel that has regions with different temperatures. An example of a currently commercially available device with the highest speed includes LightCycler from Roche. LightCycler has a system in which a sample, DNA polymerase, DNA fragments as primers and a fluorescence-labeling dye for measurement are introduced into each of a plurality of glass capillary tubes, and the temperature of a minute amount of the droplet in this capillary tube is changed by blowing hot air at the same temperatures as the temperatures required for the droplet to be changed (for example, between two temperatures of 55° C. and 95° C.), and at the same time, irradiating this glass capillary tube with excitation light for the fluorescent dye, thereby allowing measurement of the obtained fluorescence intensity.

The temperature of a sample can be changed repeatedly by these methods.

PRIOR ART DOCUMENTS

Patent Documents

[Patent Document 1] Japanese Patent Unexamined Application Publication No. 2003-107099
[Patent Document 2] Japanese Patent Unexamined Application Publication No. 2004-85323
[Patent Document 3] Pamphlet of International Publication No. 2004/101731

Non-Patent Documents

[Non-patent Document 1] Kamarck, M. E., Methods Enzymol. Vol. 151, p 150-155 (1987)
[Non-patent Document 2] Micro Total Analysis, 98, pp. 77-80 (Kluwer Academic Publishers, 1998)
[Non-patent Document 3] Analytical Chemistry, 70, pp. 1909-1915 (1998)

DISCLOSURE OF THE INVENTION

Problems to be Solved by the Invention

Although the importance of identification of the presence of CTCs is recognized in regard to cancer metastasis in clinical practice, there is no diagnostic benchmark that has been established at present using the presence of CTCs as an indicator of cancer metastasis. One of the reasons for this is that, due to CTC's diversity and scarcity, high detection sensitivity is critically required in a conventional method where the presence or absence of a scarce mutant gene is examined in a sample from withdrawn blood that is assumed as a homogeneous tissue.

Particularly until now, since analysis of gene and expression in the cell has been made without inspecting whether the fluorescence-labeled cancer cell in the blood is a part of a cell aggregation with other cells or an isolated single cell, the information acquired was the population average that includes information of other cells than the target cancer cell. Therefore, there has been a problem that no accurate information of the target cancer cell can be acquired.

Moreover, in addition to the means for collecting cells as a single cell, diagnosis needed to be carried out at a higher S/N ratio by the means for collecting cells in single units as well as the means for performing genetic diagnosis and expression analysis for a minute amount of cells after sorting and concentrating the scarce cells.

Further, with respect to the current analysis means for cells, there has been a problem that there is no means for analyzing whether or not the targeted cell is in a state of apoptosis or the like upon collecting the cell.

Furthermore, when the content of a cell that has a hard shell such as a spore of anthrax or the like is to be analyzed, there has been a problem that the content of the cell does not elute in the sample solution unless the shell of the cell can be removed by some sort of method. Therefore, in general, the cell analysis has been performed with the analysis means that incorporates the means for carrying out cultivation of a spore-forming cell for germination so that the cell's content can be eluted into the sample solution by the same procedure as that for general cells. In such cases, however, there are problems that the measurement time is delayed due to the cultivation procedure which requires at least a few hours to as long as a day, that the procedure becomes cumbersome, and that contamination may occur. In addition, as the means for analysis at high speed, there also exists a disruption method for disrupting a cell by placing a mixture of a disrupting medium such as glass balls and a sample in a disruption container and applying ultrasonic vibration or the like to the container so that they randomly collide with each other. However, there has been a problem that effective disruption efficiency cannot be obtained in spite of the generation of heat in the sample solution by the vibration, as well as a problem of efficiency in collecting the sample because when disrupting an infinitesimal amount of cells, a large amount of the sample solution and the sample are necessary.

Means for Solving the Problems

Under such circumstances, the present inventors provide a cell analyzer that enables rapid identification of the type, the state and the number (concentration) of cancer cells having metastatic capacity in the blood circulation.

Thus, the present invention provides the following device system and device.

(1) A system of devices for analyzing cells comprising:
(A) a first device for concentrating, staining and washing a cell sample solution derived from a subject;
(B) a second device for concentrating, separating and purifying the stained cell in the sample solution derived from the first device;
(C) a third device for performing gene analysis and expression analysis on the purified cell in the cell sample solution derived from the second device;
(D) a fourth device for sequentially transporting the cell sample solution from the first to third devices; and
(E) a control/analysis unit for controlling the performance of each of the devices and analyzing the cell sample,
wherein
  (a) the first device comprises:
    a chamber provided with a filter for concentrating, staining and washing the cell in the cell sample solution;
    containers for holding each of the cell sample solution, a stain solution and a wash solution; and
    a mechanism for sequentially introducing each of the solutions of each container into the chambers,
  (b) the second device comprises:
    a cell sorter chip comprising a channel through which the cell sample solution containing cells including a target cell flows, wherein the channel comprises a first channel for concentrating the cells and a second channel, branching from the first channel, for detecting the concentrated cells and sorting the target cell;
    a mechanism that applies external force to the cells flowing through each of the channels such that the cells flowing through each of the channels are concentrated in the first channel and converged toward a desired direction in the second channel; and
    an optical system comprising light irradiation means for irradiating the cells flowing through the second channel with light, and a high-speed camera that captures images of the cells at an image-capturing rate of at least 200 frames/second, and
  (c) the third device comprises:
    a reaction vessel to which the sample solution is added for reaction;
    a heat exchange vessel that exchanges heat with the reaction vessel; and
    a temperature control mechanism for controlling the temperature of the heat exchange vessel.

(2) The system of devices for analyzing cells according to (1) above, further comprising a cell disruption mechanism upstream of the third device that performs gene analysis/expression analysis of the purified cells in the cell sample solution, wherein the disruption mechanism allows the content of the cells, which are transported by the fourth device that transports the cell sample solution, to elute from the cells into the sample solution by cell disruption, and
  wherein the control/analysis unit controls each of the above members such that the cell sample solution from the second device is transported to the cell disruption mechanism by the fourth device that transports the cell sample solution, and the sample solution disrupted in the cell disruption mechanism is transported to the third device by the fourth device.

(3) The system of devices for analyzing cells according to (2) above, wherein the cell disruption mechanism comprises:
  a container for holding the cell sample;
  a disruption rolling body for disrupting the cells in the container; and
  an abrasive for disrupting the cells in the container,
  wherein the cell sample and the abrasive are added into the container, where the cell sample is disrupted by the action of the disruption rolling body whose revolving and orbital movements are strictly controlled.

(4) The system of devices for analyzing cells according to (3) above, wherein the cell disruption mechanism further comprises a rotary shaft,
  wherein the disruption rolling body rotates inside the container by being pressed from above by the rotary shaft, where the friction force and the degree of sliding between the disruption rolling body and the rotary shaft are controlled by the pressure between the disruption rolling body and the rotary shaft.

(5) The system of devices for analyzing cells according to (4) above, wherein the cell disruption mechanism comprises a mechanism that is capable of generating force of pressing the disruption rolling body in a direction perpendicular to the lateral face of the container by displacing the rotation axis of the disruption rolling body and the rotation axis of the rotary shaft.

(6) The system of devices for analyzing cells according to (4) above, wherein the cell disruption mechanism comprises a mechanism that is capable of lifting and taking away the disruption rolling body from the container by suction caused by magnetic force or electrostatic force of the rotary shaft or by difference in gas pressure.

(7) The system of devices for analyzing cells according to any one of (3) to (6) above, wherein the cell disruption mechanism is provided with a driving mechanism equipped with a plurality of containers, allowing an automatic exchange of the containers so that contamination among different cell samples can be eliminated.

(8) The system of devices for analyzing cells according to any one of (3) to (7) above, wherein the cell disruption mechanism is provided with the disruption rolling body placed inside an unused container and sealed airtight with an airtight seal so as to ensure that the container and the disruption rolling body are not contaminated during disruption of the cell samples.

(9) An image-detection-type single-cell separation/purification device, comprising:
  (i) a cell sorter chip comprising a channel through which the cell sample solution containing cells including a target cell flows, wherein the channel comprises a first channel for concentrating the cells and a second channel, branching from the first channel, for detecting the concentrated cells and sorting the target cell;
  (ii) a mechanism that applies an external force to the cells flowing through each of the channels such that the cells flowing through each of the channels are concentrated in the first channel and converged toward a desired direction in the second channel;
  (iii) an optical system comprising light irradiation means for irradiating the cells flowing through the second channel with light, and a high-speed camera that captures images of the cells at an image-capturing rate of at least 200 frames/second; and (iv) a control/analysis unit for controlling the performance of each of the above members and analyzing the image of the cell captured by the optical system.

(10) The device according to (9) above, wherein the external force is ultrasonic radiation pressure, gravity, electrostatic force or dielectrophoretic force.

(11) The device according to either one of (9) and (10) above, wherein the cell sample containing the target cell is derived from blood.

(12) The device according to any one of (9) to (11) above, wherein the target cell includes a cancer cell.

(13) The device according to any one of (9) to (12) above, wherein the control/analysis unit binarizes the image of the cell acquired from the optical system, and detect and identify each of the cells at a single cell level based on at least one indicator selected from the group consisting of a luminance centroid, an area, a perimeter, a major axis and a minor axis of the binarized image.

(14) The device according to (13) above, wherein the cells in the cell sample solution are labeled with fluorescence, the optical system further comprises a fluorescence detecting means, and information of the fluorescence images of the cells is used as an additional indicator by the control/analysis unit.

The present invention further provides the following on-chip cell sorter and on-chip cell sorter system.

(15) An on-chip cell sorter, comprising:

a sample channel and two buffer solution channels disposed on both sides of the sample channel, all having the same lengths and cross-sections, wherein the two buffer solution channels meet the sample channel at a confluence;

a central collection channel and two waste fluid channels, which are disposed downstream of the confluence, all the channels having the same lengths and cross-sections, wherein the two waste fluid channels are disposed on both sides of and branched from the collection channel;

a reservoir for a sheath solution which covers inlet openings of the upstream three channels;

a sample solution reservoir for filling with a sample, disposed within the reservoir for the sheath solution, wherein the cross-sectional ratio of the sheath solution reservoir versus the sample solution reservoir is 2:1 which corresponds to the ratio of the number of the respective channels, and the heights of the liquid levels in the reservoirs are kept even when the liquids are allowed to flow from the reservoirs;

waste fluid reservoirs and a reservoir for collected cells disposed in the downstream region, wherein the cross-sectional ratio of the waste fluid reservoirs and the reservoir for collected cells is 2:1 in the same manner as above;

a mechanism for identifying the cells, provided upstream of the confluence, comprising a high-speed camera and a mechanism for identifying the cells by fluorescence detection; and gel electrodes disposed at the confluence so as to symmetrically make contact with the confluence, wherein an electric field is applied only to a cell to be eliminated.

(16) The cell sorter according to (15) above, wherein the reservoirs of the cell sorter comprises: a plug disposed on the upper surface of the sheath solution reservoir; means for applying compressed air that penetrates through the plug; means for continuously supplying additional liquids to the liquid sheath solution reservoirs and the sample reservoir; and an electric sensor capable of measuring the heights of the liquid levels in both of the sheath solution reservoir and the reagent reservoir.

(17) The cell sorter according to (15) above, wherein the reservoirs of the cell sorter comprise individual containers for storing a reagent solution and two sheath solutions disposed at upstream inlets of the three channels respectively.

(18) An on-chip cell sorter which is an image-recognizing-type cell sorter, characterized in that a cell undergoing mitosis is selectively collected utilizing the presence or absence of the nucleus image in the cell image as a benchmark.

(19) An on-chip cell sorter system which is an image-processing-type cell sorter, characterized in that the time of single flashing per frame for each frame rate of a high-speed camera is determined by the following expression in order to prevent blurring of the image:

$$\text{Flashing time}=\text{Pixel size/Flow velocity.}$$

Effect of the Invention

According to the present invention, a minute amount of target cell in blood can be purified at a single cell level to realize accurate analyses of gene information and expression information of the target cell.

According to the present invention, whether subject cells are clustered or not (whether it is in the form of an isolated single cell or not) can be identified.

According to the present invention, whether or not apoptosis is induced in a cell can be determined.

According to the present invention, only the target cell can be separated/purified and collected in real time.

According to the present invention, only the collected cells can be subjected to determination of the cellular state of each single cell to perform genomic analysis and expression analysis for each single cell.

According to the present invention, only the collected cell can be recultivated.

According to the present invention, a cell can be purified based on the results obtained from capturing detailed information of the cell such as difference in the size of the cell and the ratio of the size of the nucleus in the cell to that of the cytoplasm.

According to the present invention, for a cell having a spore such as anthrax, a substance in the cell can be analyzed rapidly with minimum contamination.

According to the present invention, a cell capable of undergoing cell division such as a cancer cell or a stem cell in the blood can be collected by collecting a cell undergoing cell division in blood.

BRIEF DESCRIPTION OF THE DRAWINGS

FIGS. 4A-C A view schematically showing an exemplary configuration of the image-detection-type single-cell separation/purification (cell sorter) module in FIG. 2.

FIGS. 9A-13 A view schematically showing variations of the basic cell disruption mechanism shown in FIG. 8. A mechanism for ensuring adherence between the container and the rolling body is exemplified.

FIGS. 10a-h A schematic view showing various shapes of the rolling body and the rotary shaft of the cell disruption mechanism used with the present invention.

FIGS. 11a-f A figure schematically showing the whole procedure for disrupting a sample according to the cell disruption step of the present invention.

FIGS. 12A-B A conceptual diagram of an automation structure for continuously disrupting cells in the cell disruption step of the present invention.

FIG. 13 A figure schematically showing an exemplary chip configuration in the cell sorter module according to the present invention.

FIGS. 17A-13 A figure schematically showing image recognition of the process of losing a nucleus upon mitosis, which is one of the indicators for identifying cell purification in the image-detection-type single-cell separation/purification (cell sorter) module in FIG. 15.

FIG. 18 A figure schematically showing an example of the timing of light emission by a high-speed flash light source for preventing blurring of the image in the image-detection-type single-cell separation/purification (cell sorter) module.

EMBODIMENTS FOR CARRYING OUT THE INVENTION

Figure 1:
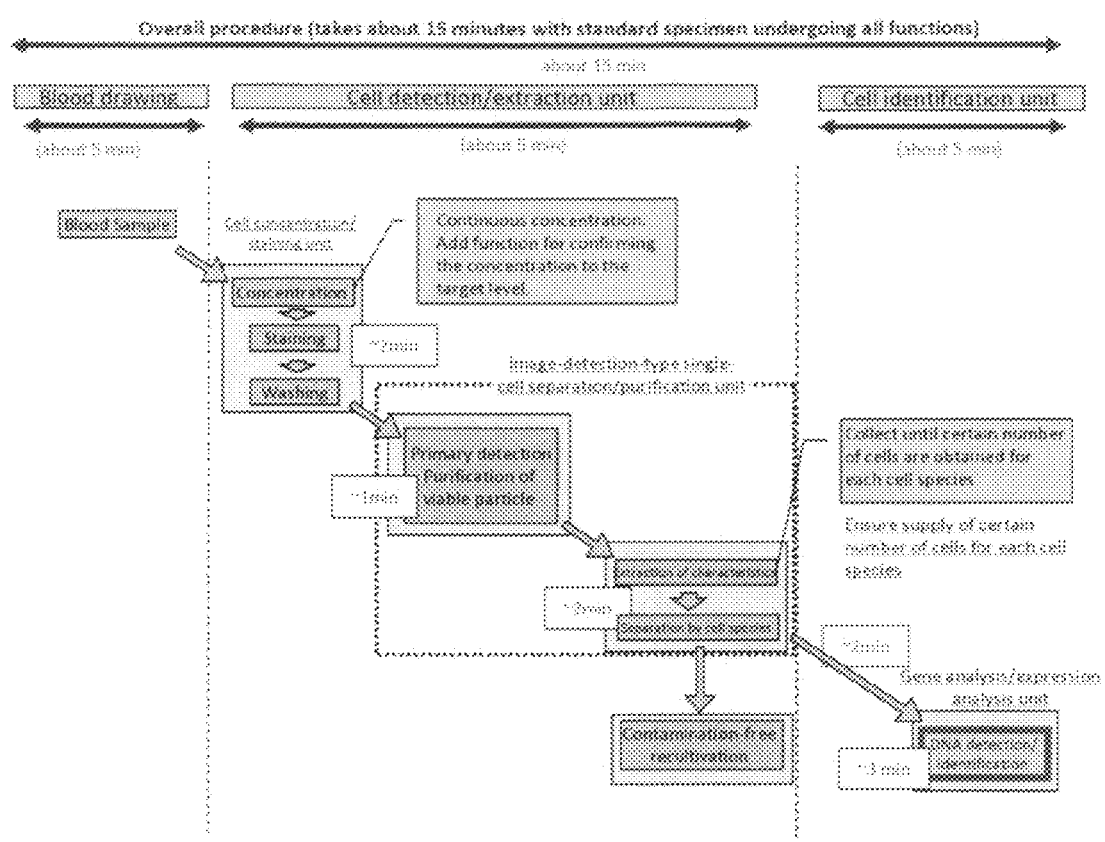
FIG. 1 A schematic view conceptually showing the whole process of a cell analysis carried out using a system of devices for analyzing cells of the present invention, and exemplary means in the device corresponding to each step.

A cell analyzer of the present invention generally comprises:
(1) a cell concentration/staining/decoloring unit that sequentially performs a process including concentration, staining with a fluorescence antibody label (or in the case where recultivation is to be performed, if necessary, a reversible fluorescence-labeled marker such as aptamer) and washing of cells;
(2) an image-detection-type single-cell separation/purification (cell sorter) unit that captures image data of cell images at about 10,000 images per second from the cells flowing through a micro flow-path formed on a chip substrate, and purifies 10,000 cells per second in real time based on the analysis results of the image information;
(3) a single-cell genomic analysis/expression analysis unit that determines the cellular state at a single cell level;
(4) a transport unit for transporting a sample solution among each of the above-mentioned units; and
(5) a control/analysis unit for controlling performance of each of the above-described units to perform the above-described analysis.

A typical embodiment of a cell analyzer of the present invention comprises the above-described three modules (1) to (3) sequentially combined in the above-mentioned order and the cells can be transported sequentially through the channels. Therefore contamination or loss of a minute amount of cells due to manipulation can be minimized.

Using the cell analyzer of the present invention, the presence or absence of a fluorescence labeling of a cell can be detected at a single cell level, and it can be determined that a fluorescence-labeled cell is an isolated unclustered single cell, and further it can be determined whether or not apoptosis is induced therein. Therefore, the cell analyzer of the present invention is capable of separating/purifying a cell based on an indicator that was unidentifiable with a conventional scattered-light-detection-type cell sorter technique.

The cell analyzer of the present invention is capable of accurately and selectively collecting cells that have been stained for each single cell, capable of confirming the cellular state (such as apoptosis) of the collected cells, and capable of analyzing gene information and expression information of each cell in conjunction with fluorescence information and cellular state information of the cell.

In the cell concentration/staining/decoloring unit described in (1) above, a minute amount of cells contained in the reaction solution sequentially sent from an upstream module with non-contact force are continuously captured and concentrated. When the cells reach a certain number, a cell-label staining solution is introduced to stain the cells, then the unbound reagent is washed away, and subsequently the cells at a certain concentration are sent forth to the next module. In this cell concentration/staining/decoloring unit, an elemental technology for capturing/concentrating a cell is used, making use of the characteristics of "dielectrophoretic force" which is generated by an alternating electric field by metal electrodes disposed in the micro channel of the cells so as to concentrate the cells.

Moreover, by the means for separating/purifying each single cell based on the results of image detection described in (2) above, detailed information of the cells, such as difference in size among the cells and the ratio of the size of the nucleus in the cell to that of the cytoplasm, is captured as image information, and the cells are purified based thereon. A high-speed camera is used for capturing the image, where the emission of light from a light source is adjusted according to the shutter cycle of the high-speed camera. The light is emitted from the light source only for a certain period of time during each period of releasing the shutter. For example, if the shutter speed is 1/10,000 second, the target cell is irradiated with light only for one-tenth of that period with the light source whose light emission can be controlled at high speed, such as an LED light source or a pulse laser light source, so that a detailed shape of the cell can be acquired.

With regard to a conventional cell sorter, when a cell sorter is mounted on a chip as the above-described separating/purifying means, the cells introduced into the cell sorter are concentrated by a separate means, for example, a centrifuge or the like, undergoing a separate concentration step. This has a problem of contamination during that process. Thus, according to the present invention, all the functions other than the optical system are equipped on the chip only in a closed environment. Specifically, it is configured to concentrate the cells on the chip, and the transport unit as well as the culture vessel for the separated cells are formed on the chip. As a result, not only contamination or loss of the cells can be prevented but also the usability is improved by simplifying the procedure and shortening the processing time. In addition, the closed environment eliminates the need for considering contamination when prevention of contamination of cells from other analyte tissue is essential, e.g., separation or clinical examination of stem cells. Thus, the present invention provides a cell separation system that enables no cross-contamination that is critical in the field of medicine, particularly in the field of regenerative medicine, by making the main parts of the cell sorter equipped on a chip and thus making it possible to have a device with complete prevention of cross-contamination.

Cells targeted for detection according to the present invention include, for example, as small as bacteria to as large as animal cells (for example, cancer cells). Therefore, the size of the cell is typically in a range of about 0.5 μm to about 30 μm. Firstly, the problem is the width of the channel (shape of cross-section) when cell concentration and separation are to be sequentially performed using a substrate with a channel incorporating both the cell-concentration function and the cell separating function being incorporated on one side of the substrate. The channels are formed on one surface of the substrate substantially in two dimensions and in a space of about 10 to about 100 μm in a thickness direction of the substrate. In regard to the size of the cell, the most typical size of the channel for a bacterium would be about 5 to about 10 μm in the thickness direction and about 10 to about 50 μm in the thickness direction for an animal cell.

Typically, the cell analyzer of the present invention comprises, in the same chip, a cell concentration unit having a function of concentrating a cell, a cell alignment unit and a cell separation/purification unit having a function of separating/purifying the cell, and an optical analysis unit for identifying and determining the separated/purified cell. Typically, an unconcentrated sample solution is introduced from one inlet to the cell concentration unit, and the sample solution is discharged from a discharge section disposed downstream from the cell concentration unit. In addition to such a basic configuration, means for applying external force to the cells in a direction toward an opening for collecting the concentrated cell provided on the sidewall of the concentration unit so as to concentrate the cells may be provided. In this case, the external force may be, but not limited to, ultrasonic radiation pressure, gravity, electrostatic force, dielectrophoretic force or the like. The arrangement employed in this case is such that the external force can be applied in a direction perpendicular to the flow direction of the sample solution in the concentration unit and toward the opening for collecting the concentrated cells.

In the cell separation/purification unit, external force is applied to the cells such that they are aligned in the middle of the channel through which they are flowing so that all of the cells can flow into one of the two branched downstream channels. Following this, external force is further applied only to the cells to be collected among the aligned cells so that the position of the flowing cells is changed and the cells are introduced into the other channel of the two branched channels only when this external force is applied. Specifically, as the external force, means for arranging cells to the node of a standing wave resulting from the ultrasonic radiation pressure can be utilized. Alternatively, means for arranging cells that comprises combined wedge-shaped electrode arrays can be employed to align the cells to the apex of the wedge-shaped electrode arrays. Alternatively, means for arranging cells that comprises a pair of cat's whisker electrodes can be employed to align the cells between the two electrode pairs. Using these means, cells can be aligned in a line without introducing a side sheath solution, and thus the above-described problem to be solved by the invention, i.e., dilution of the cell solution which has just been concentrated in the previous stage, can be solved as well.

The cell detection function of the cell analyzer of the present invention resides in the image-detection-type single-cell separation/purification unit described in (2) above. When cells are to be captured and assessed as an image, a site for observing with a CCD camera is provided upstream of a confluence of the channels, and if necessary, a cell separation region is provided downstream of the site for observing with the CCD camera. Regardless of the images, a cell passing through the channel is irradiated with laser or the like so as to detect the scattered light of the passing cells or detect fluorescence, if the cells have been modified with fluorescence, with a photodetector. Similarly, a confluence point for branching of the channels is provided as a cell separation region downstream from the detection region.

When the cells are separated at a sorting unit which is the cell separation region, and when dielectrophoretic force is used as the means for applying external force to the cells in the cell sorting unit to shift the cells, for example, a pair of comb-like electrodes is arranged in a channel so that the cells can be separated and discharged through the channel. When electrostatic force is utilized, a voltage is applied to the electrode to change the positions of the cells within the channel. In this case, since cells are generally charged negatively, they migrate toward the positive electrode.

In addition, according to the present invention, since the pressure for introducing a sample solution into a chip is the driving force for migration of a liquid, it is preferable that the pressure at a waste fluid outlet (flow outlet 213) of the cell concentration unit 215, the pressure at a purified cell outlet (cell collection unit 224) of the cell sorting unit 217 and the pressure at a waste fluid outlet (waste fluid collection unit 223) of the cell sorting unit are configured to be almost equal (see FIG. 4B). For this reason, a channel resistance adjustment unit is provided immediately before each of the outlets, for example, a narrow channel, an S-shaped long channel, etc., to adjust the pressure.

The algorithm for recognizing and separating the cells has the following features.

When an image of a cell is to be captured for evaluation, a site for observing the part of the channel is provided downstream of the confluence by a CCD camera, and the range for measurement is expanded on a plane and the cells are identified and traced through the image recognition, thereby realizing more reliable cell separation. What is important here is the image capture rate. With a camera having a commonly-used video rate of 30 frames/second, some cells may be missed in the image. A capture rate of at least 200 frames/second enables recognition of the cells flowing at a fairly high speed through the channel.

Next, with respect to the image processing technique, a higher capture rate means that image processing should not be too complicated. First, as to cell recognition, as described above, the migration speed of the cells differs with the cells, and in some cases, a cell may overtake other cell. Accordingly, the cells are numbered upon first appearance in the image frame, and thereafter the cells are handled under the same number until they disappear from the image frame. Specifically, the state of the cell images migrating in a plurality of consecutive frames is managed by numbers. The cells in each frame travels sequentially from upstream to downstream frames, where the cells among the frames are linked provided that a migration speed of a certain numbered cell recognized in the image is within a certain range. By doing so, even if some cells overtake other cells, each cell can be traced for sure.

In this way, cells can be recognized. For numbering the cells, first, a cell image is binarized to determine the centroid. The luminance centroid, the area, the perimeter, the major axis and the minor axis of the binarized cells are determined, which are used as parameters for numbering each cell. It is also beneficial for the user and therefore recommended that each of the cell images is automatically stored at this point.

Next, for the purpose of cell separation, only certain cells need to be separated from the numbered cells. The indicator for the separation may be the above-described information on the luminance centroid, the area, the perimeter, the major axis, the minor axis or the like. Other than the images, information utilizing fluorescence may be obtained by concomitantly performing fluorescence detection. In either case, the cells obtained at the detection unit are separated according to the given numbers. Specifically, the migration speed (V) of a numbered cell is calculated based on the images that are captured every predetermined time. Selecting the timing for application between (L/V) to (L/V+T) based on the cell migration speed (V), the distance from the detection unit to the sorting unit (L) and the application time (T), the cell with the targeted number can be electrically sorted for separation as the cell passes through between the electrodes.

With respect to the high-speed single-cell genomic analysis/expression analysis means in (3) above used with the present invention, in order to accomplish the above-described objective, using liquids having a high heat capacity and temperatures maintained at each desired temperature as a heat exchange media, for example, the reaction device for use in the present invention comprises a means for rapidly changing the temperature of liquids of a plurality of different temperatures and a high heat capacity, and a micro reaction vessel for performing heat exchange between the liquid of high heat capacity and the sample solution. Specifically, a reaction control device as used in the present invention comprises a micro reaction vessel having a structure and a material suitable for heat exchange, a vessel for exchanging heat for the reaction vessel by circulating the liquid at the temperature appropriate for each reaction outside the micro reaction vessel, a plurality of liquid reservoir tanks including a heat source for maintaining the temperature of the liquid to a high accuracy, a switching valve system for guiding a liquid from an arbitrary liquid reservoir tank to outside the reaction vessel so as to rapidly change the temperature of the micro reaction vessel, and a mechanism for preventing mixing of the liquids at different temperatures upon switching of the valve system.

Controlling the temperature of a reaction vessel with a refluxing liquid provides the following advantages. First, the problem of temperature overshoot can be solved. Since the temperature of a liquid constantly refluxing stays constant, the temperature of a surface of the reaction vessel and the temperature of the liquid equilibrate at once. Heat gradient is basically not generated since heat capacities of the reaction vessel and the sample are insignificant as compared to that of the refluxing liquid, and the liquid is continuously flowing even if heat is locally drawn from the liquid. Of course, the temperature of a reaction vessel does not exceed the temperature of the liquid. By continuously pouring liquids at different temperatures into vessels for exchanging heat with the reaction vessel, the temperature can be changed by 30 degrees or more within 0.5 seconds.

Hereinafter, embodiments of the present invention will be described in more detail with reference to the drawings, however, they are merely exemplification and the scope of the present invention should not be limited to these embodiments.

(System Configuration of Cell Analyzer)

FIG. 1 illustrates an example of a procedure from collection to analysis of a sample from the blood using a cell analyzer of the present invention.

A blood sample collected from a patient is directly introduced into a cell concentration/staining unit. Here, only cellular components are extracted from the blood, to which a fluorescence-labeling agent such as a fluorescent cancer marker is added for reaction with the cell sample. The excess unreacted fluorescence-labeling agent is washed away and the sample is introduced into an image-detection-type single-cell separation/purification unit in a form of a solution of an optimal cell concentration for the following image-detection-type single-cell separation/purification unit.

Next, as a primary detection in the image-detection-type single-cell separation/purification unit, the presence or absence of fluorescence emission is determined for each single cell based on the fluorescence label. In this way, whether or not the cell is a target cell can be determined by a conventional labeling technique. Besides that, images taken with a high-speed camera are analyzed in real time with respect to target cells which emit fluorescence so that it can be determined: 1) whether the fluorescence-emitting cell is an isolated cell or whether it is forming a cell aggregation with other cells; and 2) whether the fluorescence-emitting cell is in a healthy state or in a state such as apoptosis where the shapes of the cellular nucleus and the cell are deformed, and consequently a healthy cell or an apoptotic cell can be collected in accordance with the intended purpose and introduced into the next stage, i.e., a high-speed, minute-amount-responsive gene analysis/expression analysis unit such that gene analysis and expression analysis can be carried out separately for respective cell forms. In particular, when the cells are forming a cell aggregation, they are not collected even when a fluorescence-emitting cell is present because cells other than the target cell may be contained.

With respect to the cells identified and purified at this stage, the purified cell may be recultivated under a contamination-free environment, other than being introduced into the gene analysis/expression analysis unit.

The gene analysis/expression analysis unit is provided for identification of the gene or identification of expression with respect to the cell introduced in a minute amount, through identifying the cell as identical cell at a single cell level or at a level of a population of identical cells based on the information from the image-detection-type single-cell separation/purification unit.

Figure 2:
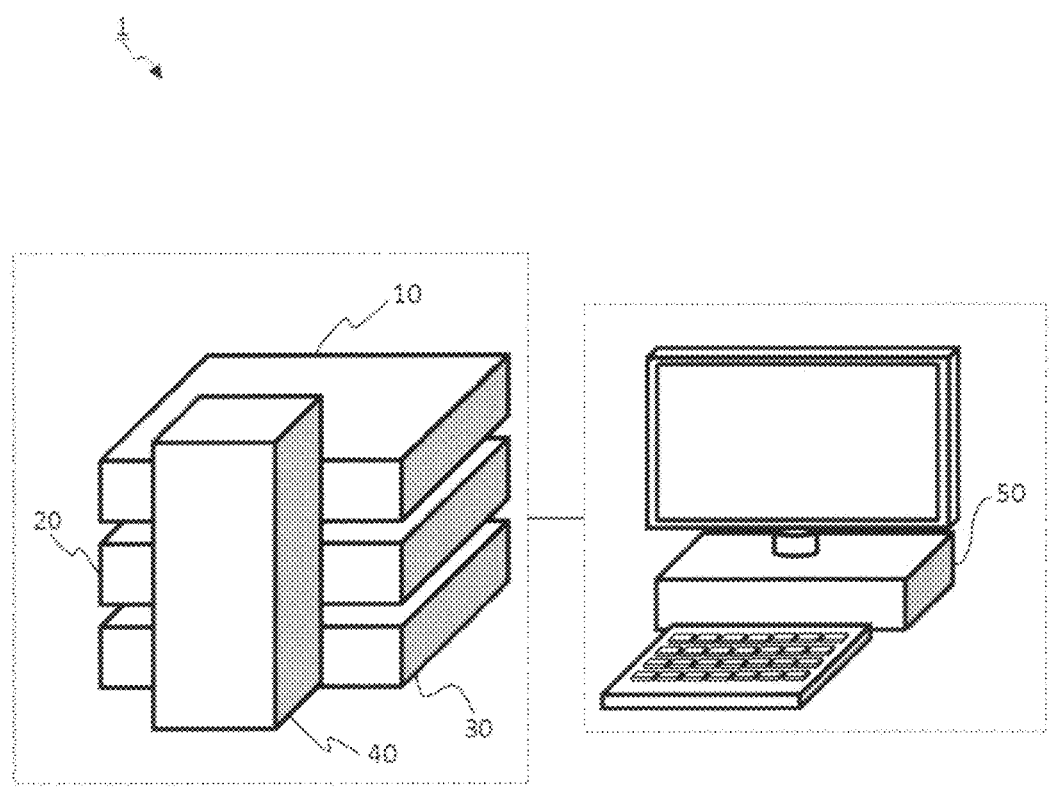
FIG. 2 A view schematically showing an example of the whole configuration of the system of devices for analyzing cells of the present invention in FIG. 1.

FIG. 2 shows an example of overall image of a system of devices for analyzing cells 1 for realizing the procedure shown in FIG. 1. The device system 1 is provided with a concentration/staining/decoloring module 10 for introducing a blood sample and performing pretreatment on cells, an image-detection-type single-cell separation/purification module 20 for identifying/purifying each single cell, a single-cell genomic analysis/expression analysis module 30 for performing gene analysis and expression analysis of the purified cells, a transport module 40 for transporting the sample among the modules, and a control/analysis module (computer) 50 for controlling the performance of the whole system and analyzing the analysis results.

FIGS. 3 to 6 each show an exemplary configuration of each of the modules of the example shown in FIG. 2.

Figure 3:
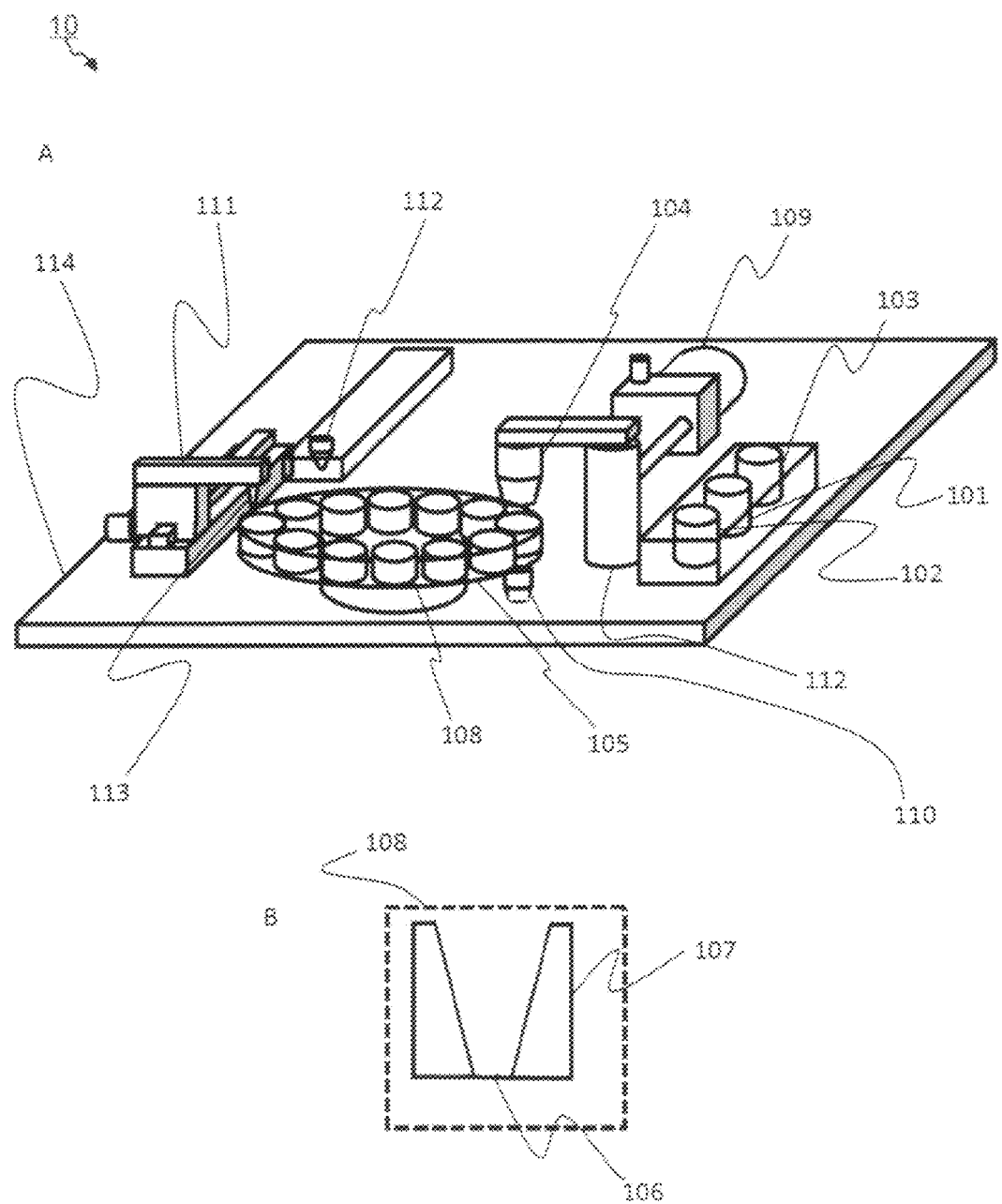
FIGS. 3A-B A view schematically showing an exemplary configuration of the cell concentration/staining/decoloring module in FIG. 2.

Firstly, FIG. 3 shows an exemplary configuration of the cell concentration/staining/decoloring module 10 for introducing a blood sample derived from a subject (e.g., cancer patient)

and performing pretreatment on the cell. In the example shown in FIG. 3, the cell concentration/staining/decoloring module 10 is disposed integrally on a chassis 114. In the module, containers or reservoirs (101, 102, 103) for retaining each solution of a cell sample, a stain agent or a wash agent are disposed, and the solutions can be introduced into a chamber 107 having a concentrating/decoloring filter 106 on the bottom surface (together forming a concentrating chamber 108) disposed on a turntable 105 by a dispensing head 104 attached to a rotating arm 112. First, a cell sample such as blood is introduced into the concentrating chamber 108, and the liquid component is discharged into a waste fluid collecting tube 110 via the filter by a pressure pump 109, thereby concentrating the cells. Then, a dispensing head 104 is used to introduce a stain solution for reaction for a certain period of time, and again the stain solution is discharged by the pressure pump 109. Next, the decoloring agent is introduced into the concentrating chamber 108 to wash and discharge excessive stain agent. Subsequently, a diluent which generally also serves as a wash agent is introduced to dilute the cells to a desired concentration, and the cells are introduced into the collecting tube 112 via a collecting head 111 that has a collecting chip 113 at the distal end.

FIG. 4 shows an exemplary configuration of an image-detection-type single-cell separation/purification module 20 for identifying and purifying each single cell. As can be appreciated from FIG. 4A, the image-detection-type single-cell separation/purification module 20 is provided with an optical system comprising a light source 201, a mirror 202, a condenser lens 203, a dichroic mirror 204, a filter 205, a photomultiplier for fluorescence detection, a high-speed camera 207 and a photodiode 208 used for scattered light detection, and a cell sorter chip 209 for introducing a cell sample. In the module shown in FIG. 4A, with respect to the cells passing through the cell sorter chip 209, multiple information can be detected at the same time with a light source 201 such as a pulse laser or a high-intensity LED light source, a photodetection element 208 such as a photodiode that can detect the passing cells by scattered light, a highly sensitive photodetection element 206 such as a photomultiplier for detecting fluorescence, a high-speed camera 207 and the like. With respect to the irradiation light from the light source, continuous light may be used to irradiate. However, in order to enhance spatial resolution of the image without blurring, pulsed light can be emitted in synchronization with the shutter cycle of the high-speed camera 207 to capture an image with a higher temporal resolution in a shorter time of light irradiation.

Needless to say, image processing may be used in combination with processing of fluorescence or scattered light. The image data acquired with the high-speed camera 207 can be displayed onto a monitor of the computer 50 for observation by the user. When multiple types of fluorescence are to be observed, the filter 205 is appropriately adjusted so as to allow transmission of multiple types of excitation light, while the cells are irradiated with light with a wavelength selected so as not to overlap the fluorescence wavelength used for fluorescence detection at the downstream stage, and multiple apparatuses, i.e., a dichroic mirror 204, a filter 205 and a fluorescence detector 206, can be combined in accordance with the type of fluorescence to be observed. Using this configuration, the data resulting from observing the fluorescence of a cell image can also be used.

The algorithm for recognizing and separating the cells has the following features.

When the cells are to be captured as an image, a site is provided downstream of the confluence for observing the channel by a CCD camera, the measurement range is expanded on a plane and the cells are identified and traced through image recognition, thereby realizing more reliable cell separation. What is important here is the image capture rate. With a general camera having a video rate of 30 frames/second, some cells may be missed in the image. A capture rate of at least 200 frames/second enables recognition of the cells flowing at a fairly high speed through the channel.

Then, with respect to the image processing technique, a higher capture rate means that image processing should not be too complicated. First, as to cell recognition, as described above, the migration speed of the cells differs with the cells, and in some cases, cells may overtake other cells. Accordingly, the cells are numbered upon first appearance in the image frame, and thereafter the cells are handled under the same number until they disappear from the image frame. Specifically, the state of the cell images migrating in a plurality of consecutive frames is managed by the numbers. The cells in each frame travels sequentially from upstream to downstream frames, where the cells among the frames are linked provided that a migration speed of a certain numbered cell recognized in the image is within a certain range. By doing so, even if some cells overtake other cells, each cell can be traced for sure.

In this way, cells can be recognized. For numbering of the cells, firstly, the cell images are binarized and the centroid is determined. The luminance centroid, the area, the perimeter, the major axis and the minor axis of the binarized cells are determined. These parameters are used to number each cell. Automatic storing of each cell image at this point is beneficial for the user and thus recommended.

Next, for use in cell separation, only certain cells have to be separated from the numbered cells. An indicator for separation may be the information such as the luminance centroid, the area, the perimeter, the major axis or the minor axis as described above, or information utilizing fluorescence obtained by concurrently performing fluorescence detection independently from the images. In either case, the cells obtained at the detection unit are separated based on the numbers. Specifically, the migration speed (V) of a numbered cell is calculated from the images that are captured every predetermined time. Based on the cell migration speed (V), the distance from the detection unit to the sorting unit (L) and the application time (T), timing for application can be set to (L/V) to (L/V+T) so that the cell with the targeted number can electrically be sorted for separation when the cell just passes through between the electrodes.

An exemplary configuration for separation and purification of a cell is as follows. The configuration includes a series of finely fabricated channels deployed on a flat chip in a two-dimensional manner for concentrating, arranging and purifying cells which are contained in a sample solution introduced, and means for applying force to the cell incorporated into the chip.

A cell separation/purification module is configured on the chip. FIG. 4B schematically shows an example of such cell sorter chip 209 configured on the chip. A micro flow-path 211 is formed within a chip substrate 210, and an aperture for communication with the channel is provided on the upper surface of the substrate as a feed port for a sample or a buffer (medium). A channel can be made by so-called mold injection where a plastic such as PMMA is poured into a mold. Alternatively, it may be made by adhering a plurality of glass substrates. The size of the chip is, for example, but not limited to 50×70×1 mm (t). For observation of a groove or aperture calved within the chip or the cells flowing through the channel or the wells by a high-powered optical microscope, a laminated film with a thickness of 0.1 mm, for example, is thermally compressed when PMMA plastic is used; and similarly, glass with a thickness of 0.1 mm is optically adhered when glass is used. For example, an objective lens having a numerical aperture of 1.4 and a magnification of 100 can be used to observe the cells flowing through the channel via a laminated film with a thickness of 0.1 mm. In the case where a plastic is used, a plastic with high translucency can be used to allow observation from above the top surface of the chip substrate 210 as well. A cell envisioned by the present invention is as small as a bacterium and as large as an animal cell such as a cancer cell. Therefore, the size of the cell is typically in a range of about 0.5 μm to about 30 μm, although it is not strictly limited to this range and a cell with any size can be used as long as the present invention can effectively be carried out. In the case where cell concentration and separation are to be sequentially performed by a channel that is incorporated on one side of a substrate, the first problem is the width of the channel (shape of cross-section). Furthermore, since the channel 211 is formed in a thickness direction of the substrate and substantially in two dimensions on one surface of the substrate typically in a space of about 10 to about 100 μm. In regard to the size of the cell, the most appropriate size of the channel for a bacterium would be about 5 to about 10 μm in the thickness direction, and for an animal cell, about 10 to about 50 μm in the thickness direction.

On chip 209, a sample solution is first introduced into a micro flow-path 211 from a flow inlet 212 by a syringe pump or means that does not generate a current, such as air pressure, for introducing a cell. The cell-containing sample solution introduced into the micro flow-path 211 flows downstream along the flow line of particle flow 218 prior to application of an external force toward a flow outlet 213 and discharged. Means for applying external force to the cells is introduced to concentrate the cells toward a concentrated cell solution inlet 214 disposed on a part of the sidewall of the micro flow-path 211. With this applied external force, the cells are concentrated along the flow of cells 219 so as to be introduced into the concentrated cell solution inlet 214 after the cell solution is concentrated to a high concentration of 100 time or more of that of the cells introduced into the flow inlet 212.

The external force applied to the cells may be ultrasonic radiation pressure, gravity, electrostatic force or dielectrophoretic force. For example, if an ultrasonic radiation pressure is to be used, a traveling wave of ultrasonic is generated in a direction perpendicular to the flow of the sample solution and toward the concentrated cell solution inlet 214. With this ultrasonic radiation pressure, the flow 219 of cells can be generated. With respect to the means for introducing ultrasonic, a PZT piezoelectric element may be adhered to the surface of the chip 209; or in order to generate surface acoustic wave on a cell concentration unit 215, a comb-like electrode array may be disposed on a surface of a piezoelectric element and then the element can be attached on the surface of the cell concentration unit 215 so that the emitted ultrasonic wave propagates to the cell concentration unit 215. If gravity is to be used, the spatial configuration of the chip 209 can be adjusted such that the gravity is perpendicular to the flow of the sample solution and that the direction of the concentrated cell solution toward the concentrated solution inlet 214 becomes the direction of the gravity. Alternatively, the chip 209 may be disposed on a rotatable disk such that the gravity is perpendicular to the flow of the sample solution and that the direction of the concentrated cell solution toward the concentrated solution inlet coincides with the radial direction of the disk. If electrostatic force is to be used, an electrode is disposed on the sidewall of the micro flow-path 211 so that the cells are subjected to the external force and directed toward the sidewall. In this case, the type of the charge applied can be determined according to positive or negative electric potential of the cell surface of the target cell. If electrostatic force is to be generated, however, bubbles are produced from the electrode once the electric potential of the surface of the electrode generating a current exceeds a certain level of electric potential such as the peroxidation potential or the perhydrogenation potential, which results in very poor voltage to be applied. Therefore, the channel length of the micro flow-path 211 needs to be adjusted flexibly according to the type and intensity of the external force applied to the cells. For example, the length has to be sufficiently long in the case of electrostatic force. If dielectrophoretic force is used as the external force, an electrode can be disposed in the cell concentration unit 215 such that dielectrophoretic force is applied in a direction perpendicular to the sample solution and that the concentrated cell solution is directed toward the concentrated solution inlet 214.

Next, as shown in FIG. 4C, the concentrated cell solution introduced in the concentrated solution inlet 214 is aligned to make a line along the flow in the solution at a converging section 216. Specifically, dielectrophoretic force or standing wave mode of ultrasonic radiation pressure is provided as the means for generating external force to attract the cells to the middle part of the channel of the converging section 216. The linearly-aligned cells in the middle are measured to determine the type of each cell at a cell detection region 218 arranged upstream of a cell sorting unit 217, and then the cells are guided to either one of the two downstream sites, a first flow outlet 221 or a second flow outlet 222, branching from a cell sorting unit junction 220, by the presence or absence of external force applied in a direction perpendicular to the flow from upstream to downstream.

As one example of an actual configuration of the converging section 216, when external force is realized by dielectrophoretic force, an electrode arrangement may be alternately-arranged wedge-shaped electrodes (V-shaped comb-like electrodes for convergence) 225 where an alternating voltage is applied to the contact point of the V-shaped comb-like electrodes for convergence so that external force is applied to the cells toward the apex of this wedge. As a result, cells can continuously be concentrated at the apex of the wedge. What is important for the electrodes in this example is the arrangement of the electrodes in the channel, i.e., a comb-like electrode array, where they make an angle towards downstream, have a sharp, not blunt, apex, and make an axially symmetric shape. By arranging so, the cells to which dielectrophoretic force is applied are guided and aligned toward the sharp apex of the electrodes, even under repulsive force or attractive force, due to the resultant force of the force that carries the cells downstream along the flow and the force applied on the cells toward the sharp apex. In other words, by arranging a sharp apex of an electrode array at a site desirable to concentrate the cells in the channel, the cells will gather to the sharp apex due to the force resulting from the force leading downstream along the flow and the dielectrophoretic force toward the sharp apex.

Figure 5:
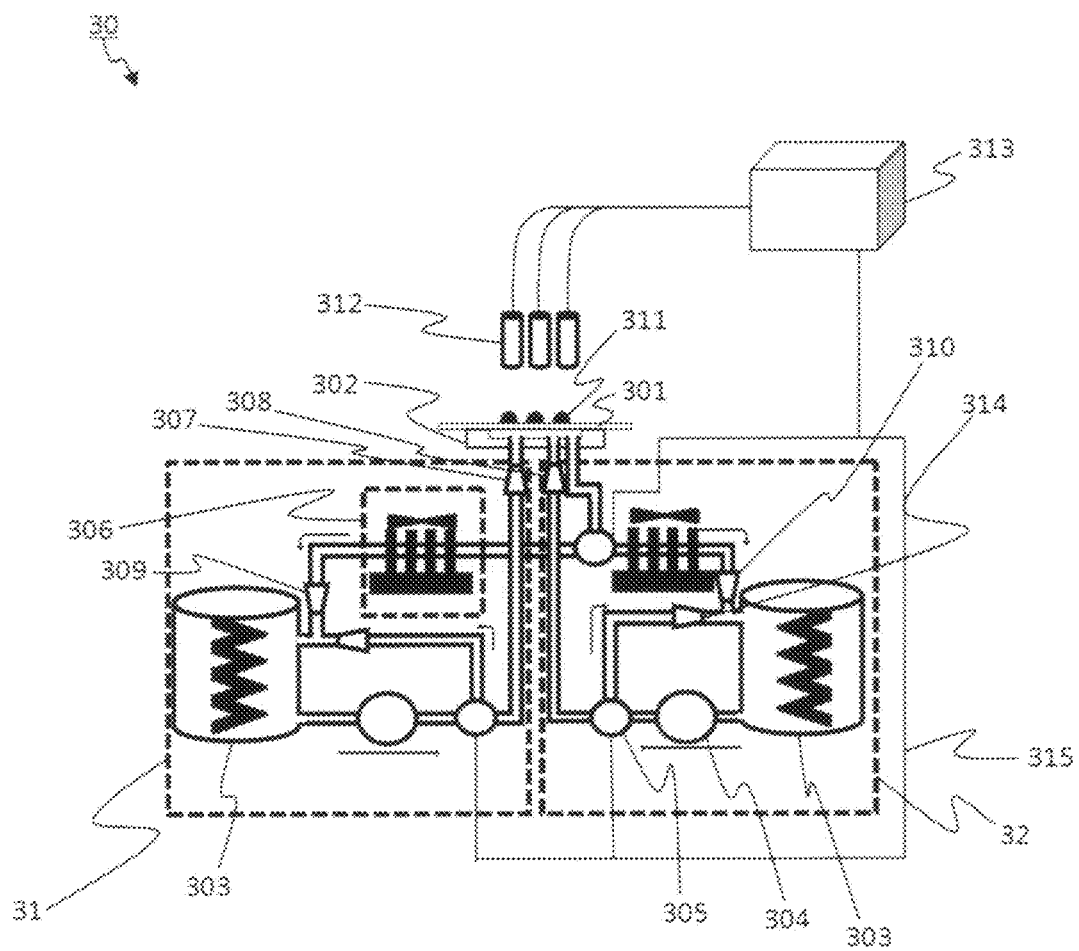
FIG. 5 A view schematically showing an exemplary configuration of the single-cell genomic analysis/expression analysis module in FIG. 2.

FIG. 5 illustrates an exemplary configuration of a single-cell genomic analysis/expression analysis module 30 for performing gene analysis and expression analysis of a purified cell. A reaction vessel 301 is made of an aluminum, nickel or gold thin plate that has a plurality of dents. The thickness of the thin plate at the dent region is about 10 to 30 micrometers, while the thickness of the region between the adjacent dents is made to lie between 100 to 500 micrometers to ensure the total strength. A reaction vessel 301 is secured on a bottom surface of a square or circular reaction vessel frame, which can easily be detached from a heat exchange vessel 302 for the reaction vessel. The liquid introduced into the heat exchange vessel 302 for the reaction vessel is heated by a heat source arranged inside a liquid reservoir tank 303. In order to rapidly draw heat from the surface of the heat source and to even out the temperature inside the liquid reservoir tank 303, an agitation mechanism is provided. The liquid in the liquid reservoir tank is guided through the channel by a pump 304. The liquid is guided to the heat exchange vessel 302 for reaction vessel by a switching valve 305 or directly returns back to the liquid reservoir tank 303 as guided by the bypass channel. If necessary, an auxiliary temperature control mechanism 306 is provided to slightly control the temperature of the liquid to restrain temperature fluctuation inside the liquid reservoir tank 303. As a basic configuration, the heat exchange vessel 302 for reaction vessel comprises inlet A (307) and inlet B (308) for introducing liquids at different temperatures. The inlets should be prepared as many as the desired number of temperatures to be changed for the sample solution, and thus inlets at two or more temperatures should be prepared. For example, three inlets are prepared when 3-temperature system needs to be achieved, and the number is not limited to two as shown in the present example. In order to return the liquid of the heat exchange vessel 302 for the reaction vessel to the liquid reservoir tank 303, a plurality of outlets, outlet A (309) and outlet B (310), are provided. The number of the outlet is not limited to two. Various shapes of reaction vessels can be used, and reaction vessels A, B, C and D are shown as part of the examples. Here, the liquid of the heat exchange vessel 302 for the reaction vessel may be water, or a liquid having larger heat capacity and lower viscosity, such as liquid ammonia. A liquid having a higher boiling point than that of water can be used as the liquid of the heat exchange vessel 302 for the reaction vessel so as to ensure the sample solution to be 100° C. or a liquid having a lower freezing point than that of water can be used to ensure change in the temperature while preventing solidification of the liquid circulating through the device as low as freezing point of water.

An optical window that transmits excitation light and fluorescence of a fluorescent dye is provided in the reaction vessel frame so that a change in the fluorescence intensity of the fluorescent dye in the sample solution that changes according to the reaction of a sample solution 311 in the reaction vessel 301 can be measured for each of one or more reaction vessels 301. Moreover, a fluorescence detector 312 is provided to measure change in the measured fluorescence intensity of the reaction vessel 301 with time. In an example shown in FIG. 5, each of the plurality of fluorescence detectors 312 is provided with an excitation light irradiation mechanism and a fluorescence detection mechanism so that PCR amplification information that differ among the plurality of reaction vessels 301 on which different primers or different sample solutions are dropped can be measured independently. The fluorescence intensity data captured with the fluorescence detector 312 is recorded by a control/analysis unit 313 which has a function of estimating DNA content or mRNA content in a sample solution obtained by PCR reaction. Furthermore, the control/analysis unit 313 also obtains switching information of the switching valve 305 and has a function of estimating whether the temperature of the sample solution 311 has reached an aimed temperature after valve switching based on the change in the fluorescence intensity with time, and also has a mechanism for controlling valve switching based on the results. This estimation is made utilizing the fact that quenching of fluorescence based on the motion of water molecules that is universal feature of a fluorescent dye depends on the liquid temperature and the change in the fluorescence intensity with unit time becomes smaller or zero. This is particularly effective in confirming the achievement of a high temperature for denaturing DNA.

In this example, each of the reaction vessels 301 is provided with one detector. However, a combination of a light source for fluorescence excitation and a camera capable of quantitatively detecting fluorescence such as a cooled CCD camera may be used to measure change in the fluorescence intensities of a plurality of reaction vessels. Alternatively, when the number of detectors used is less than the number of the reaction vessels 301, a mechanical driving mechanism that can move along the X-Y plane at high speed can be combined with a detector so as to measure the fluorescence intensities of all reaction vessels.

A reagent necessary for the reaction is conveniently lyophilized. The lyophilized reagent may be prepared on the bottom of the reaction vessel. A plug-like lyophilized reagent may be formed inside a dispensing chip used for dispensing a sample, so that the reagent can be dissolved in the sample by moving the sample up and down. Alternatively, a lyophilized reagent may be formed on the surface of a fiber ball made of a bundle of nylon fibers, so that it can be inserted into the reaction vessel and agitated in the sample to dissolve the lyophilized reagent.

Since it is inconvenient to directly handle the reaction vessel 301 made of a thin membrane, the reaction vessel 301 is conveniently secured to a reaction vessel frame. The reaction vessel frame is preferably formed with a thermal insulating material such as polystyrene, polycarbonate, PEEK, acrylic or the like, and the contact area with the reaction vessel 301 is preferably minimized for rapid and highly accurate increase and decrease in the temperature of the reaction vessel 301. In order to attach the reaction vessel 301 to the heat exchange vessel 302 for the reaction vessel, the surface of the reaction vessel frame may be threaded so that the frame can be screwed in. In order to retain water tightness, the aperture is preferably sealed. Alternatively a tapered reaction vessel frame may be employed for attachment with pressure only.

Next, a specific example of the switching mechanism of the valve will be described. Inlet valves A and B for introducing a liquid into the reaction vessel 301 and outlet valves A and B for guiding the liquid outside are provided. The liquid introduced from the inlet valve A returns to a liquid reservoir tank via the outlet valve A while the liquid introduced from the inlet valve A returns to another liquid reservoir tank via the outlet valve B. By alternately switching these two states, the sample in the reaction vessel can be subjected to reaction. According to a more preferable method for switching valves, in addition to the above-described two states, the inlet valve B and the outlet valve A or the inlet valve A and the outlet valve B are released at the same time for a moment, so that liquids at different temperatures can be prevented from being mixed with each other and controlling the temperature of the liquid reservoir tank for each system becomes easier. As a condition for performing PCR, for example, a mixture of a reaction buffer 1.0 µL, 2 mM dNTP (dATP, dCTP, dGTP, dTTP) 1 µL, 25 mM magnesium sulfate 1.2 µL, 10% fetal bovine serum 0.125 SYBR Green 10.5 two types of primers each 0.5 µL, sterilized water 3.725 µL, KOD plus polymerase 0.25 µL and genomic DNA 1.0 µL may be used. With respect to the temperature conditions, measurement can be carried out through 40 cycles of the following temperature change: first, 95° C. for 10 sec., then 95° C. for 1 sec. and 50° C. for 3 sec.

Figure 6:
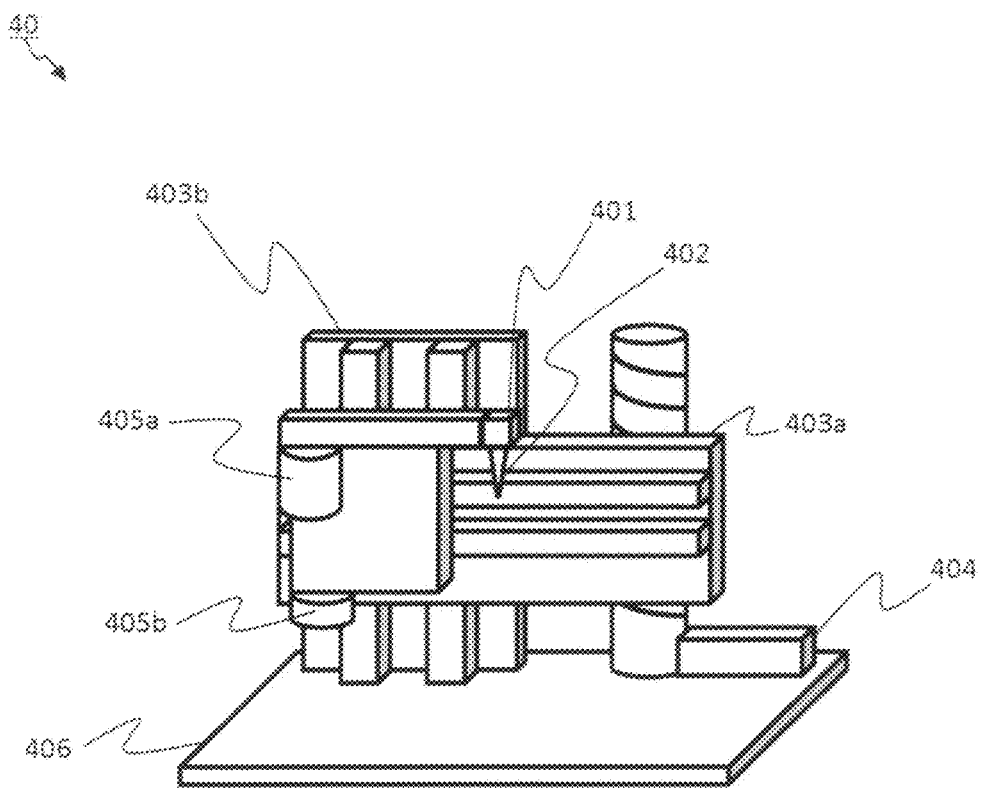
FIG. 6 A view schematically showing an exemplary configuration of the transport module in FIG. 2.

FIG. 6 shows an exemplary configuration of a transport module 40 for transporting a sample between the modules.

The configuration comprises a dispensing head 401 and a dispensing chip 402 for communicating a liquid among the modules arranged on a chassis 406, and further comprises a function of controlling the position of the dispensing head 401 along the X-Y plane with a z-axis travel guide 403 and a z-axis travel motor 404 for controlling the height of the dispensing head in the z-axial direction and an arm rotary motor 405 as a mechanism for rotating the arm.

Figure 7:
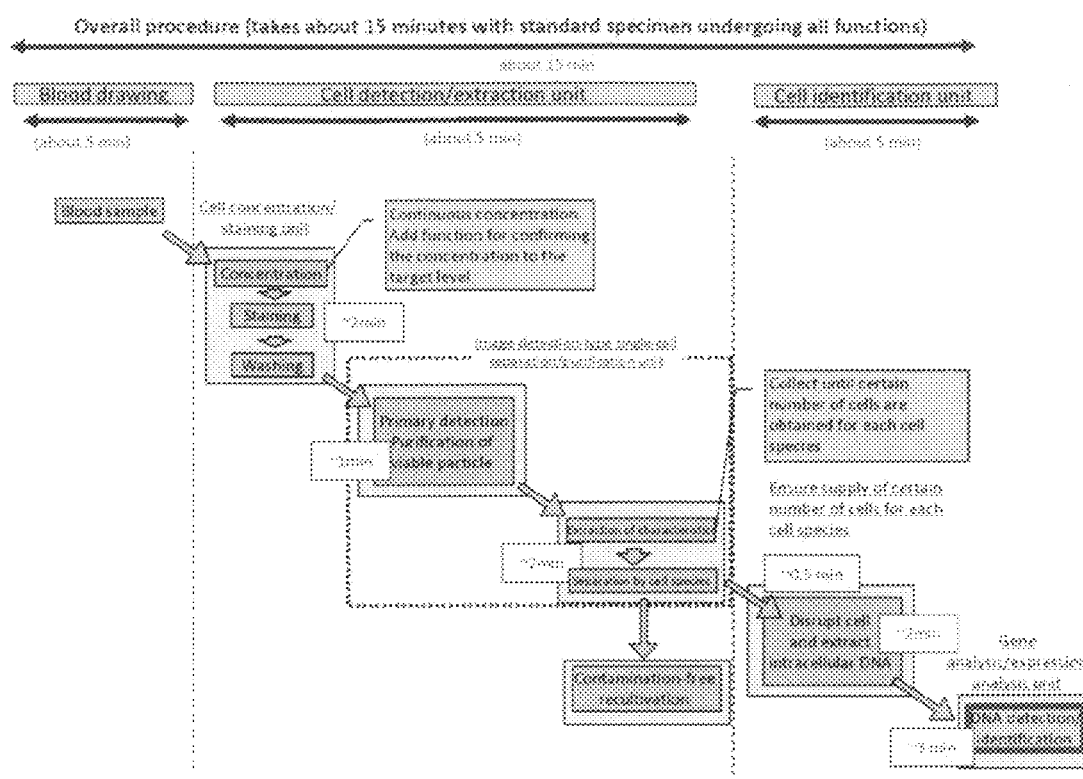
FIG. 7 A schematic view conceptually showing the whole process that includes a cell destructing step in an cell analysis using the system of devices for analyzing cells of the present invention, and exemplary means in the device corresponding to each step.

FIG. 7 illustrates an exemplary procedure from collection to analysis of a sample, among cell analyses performed using a cell analyzer of the present invention, in which, for a sample whose nucleic acid components in the cell do not easily elute in the sample solution due to the shell covering the cell (e.g., a spore of anthrax), a procedure for disrupting the shell covering the cell is introduced before the procedure of expression analysis of the cell. By adding this cell disruption procedure, the present cell analyzer becomes capable of performing analysis for cells such as a spore of anthrax in exactly the same manner as the above-described means for analyzing the blood cells.

Figure 8:
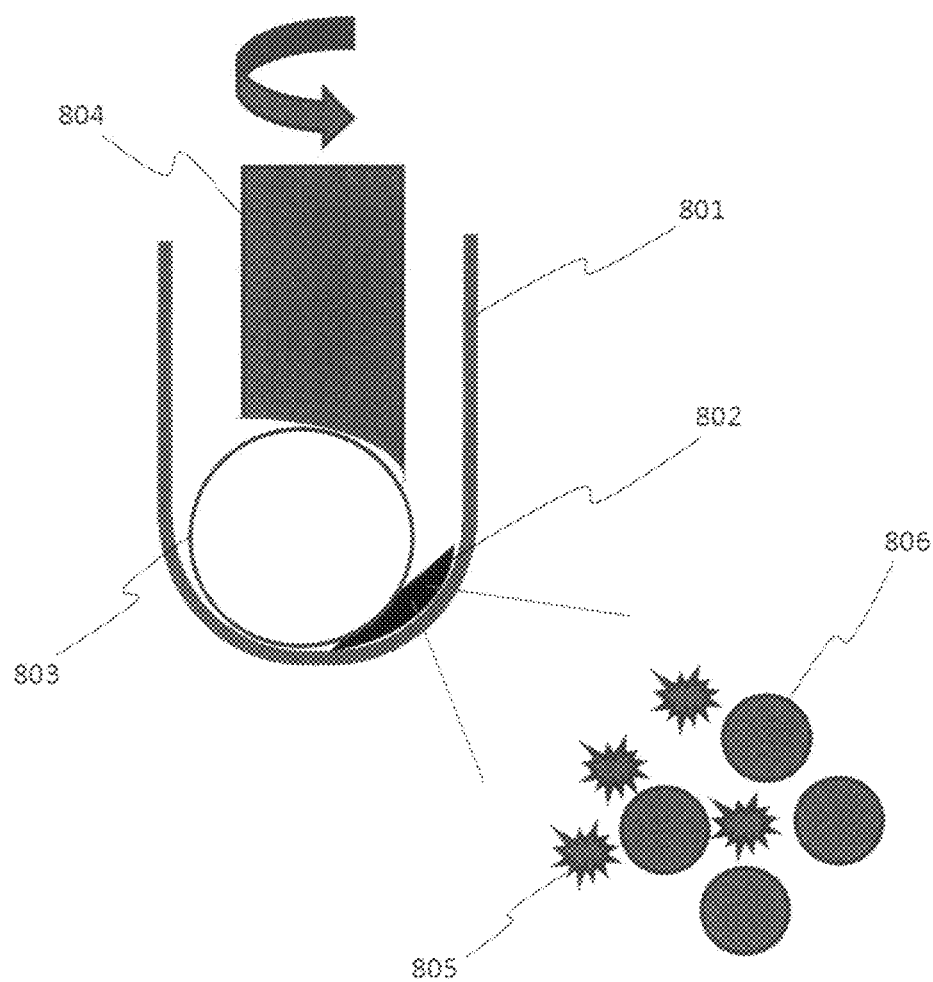
FIG. 8 A figure schematically showing an example of the disruption mechanism comprising a container, a rolling body and a rotary shaft, which is used in the step for destructing the cell among the steps shown in FIG. 7.

FIG. 8 schematically shows an example of a basic structure for automatically disrupting a shell such as a spore covering a cell in a minute amount of sample in order to analyze intracellular gene and expression information for the cell having a spore such as anthrax. A minute amount of sample 802 is dispensed into a container 801, and a disruption rolling body 803 is placed inside the container 801. In order to rotate the rolling body 803 inside the container 801, the rolling body 803 is pressed against the container 801 with the rotary shaft 804. The rolling body 803 revolves and orbits inside the container so that a sample 805 in a minute amount of sample is ground with an abrasive 806. At the end of the step, the rolling body 803 is removed so that the processed sample 805 can easily be collected. Since the rolling body 803 and the container 1 have simple structures, there is no problem in treating them as disposables.

FIG. 9 schematically shows variations of the basic cell disruption mechanism shown in FIG. 8. In order to disrupt a sample at a high efficiency, the rolling body needs to make close contact with the container. In an example shown in FIG. 9A, a container 811 including a rolling body 810 is held in a flexible structure 812 such as rubber. Since a tip part 814 of a shaft 813 is cut diagonally, when the shaft 813 is pressed against the rolling body 810, the rolling body 810 presses the container 811 in downward and lateral directions, by which the pressure flexible structure 812 is deformed to absorb the pressure. As a result, a sample can be disrupted while maintaining close contact between the rolling body 810 and the container 811 without giving an excessive stress to the rotary shaft 813. As shown in FIG. 9B, a spring mechanism 815 that deforms in vertical and lateral directions may be incorporated in the rotary shaft as a technique for releasing stress.

Figure 10:
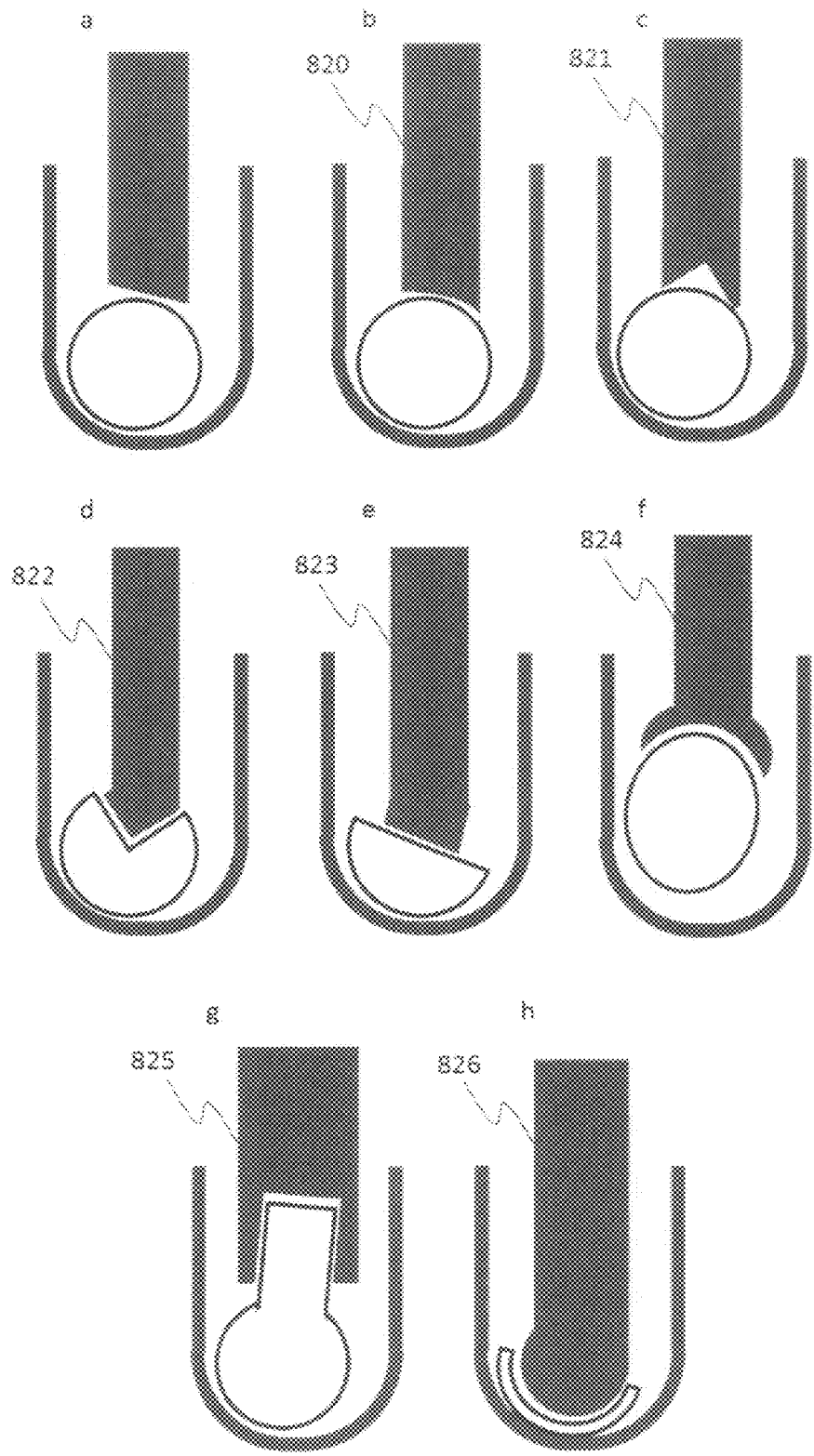

FIG. 10 shows possible rolling bodies and rotary shafts in various shapes that can be used in a cell disruption mechanism of the present invention. Other than a diagonally cut shaft tip (FIG. 10a), it may be a gently-curved scoop (FIG. 10b) or a mortar shape (FIG. 10c). The rolling body does not have to be a sphere and may take a structure so that the shaft and the rolling body gently engage with each other (FIG. 10d). A rotary shaft diagonally cut in a hemispherical shape may be used to rotate the rolling body (FIG. 10e). In addition, an oval-shaped rolling body (FIG. 100 or a protruding structure that engage with the rotary shaft (FIG. 10g) are also possible. A dish-like rolling body can also be rotated with a shaft (FIG. 10h).

Figure 11:
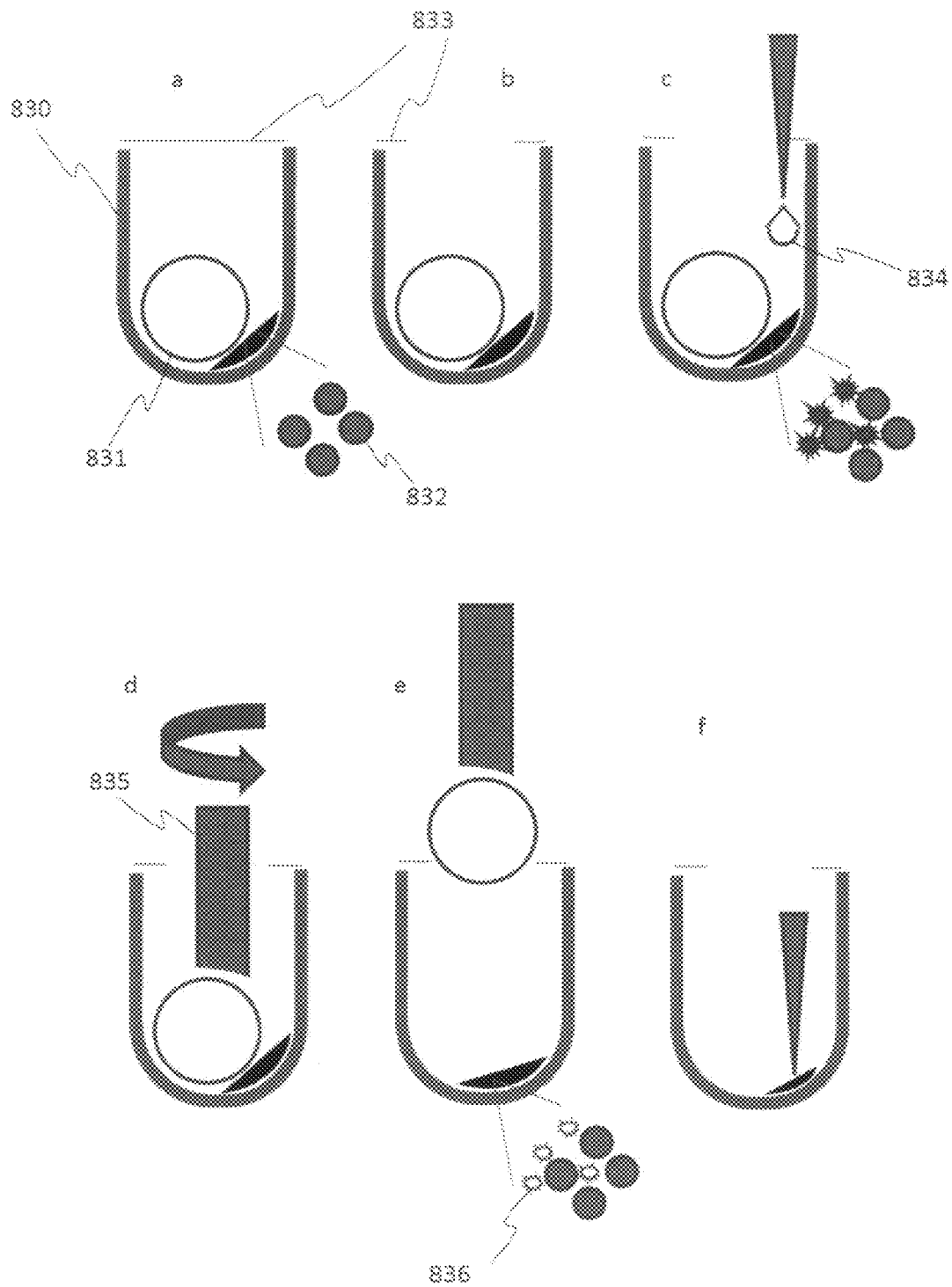

FIG. 11 shows an exemplary cell disruption step according to the present invention. A rolling body 831 and an abrasive 832 are enclosed in a container 830 (FIG. 11a). Immediately before disruption, a seal 833 is torn away (FIG. 11b), and a sample 834 containing cells is dispensed into the container 830 (FIG. 11c). The rolling body 831 is rotated by pressing it with a rotary shaft 835 (FIG. 11d) so that the cells in the sample are disrupted with the abrasive 832 and components 836 are eluted (FIG. 11e). At the end of the disruption operation, the rolling body 831 is removed from the container 830 so as to facilitate collection of the sample (FIG. 11f). The rolling body can be removed by utilizing negative pressure, magnetic force or electrostatic force, and such mechanism may be incorporated in the rotary shaft. Of course, a customized mechanism may be prepared separately.

Figure 12:
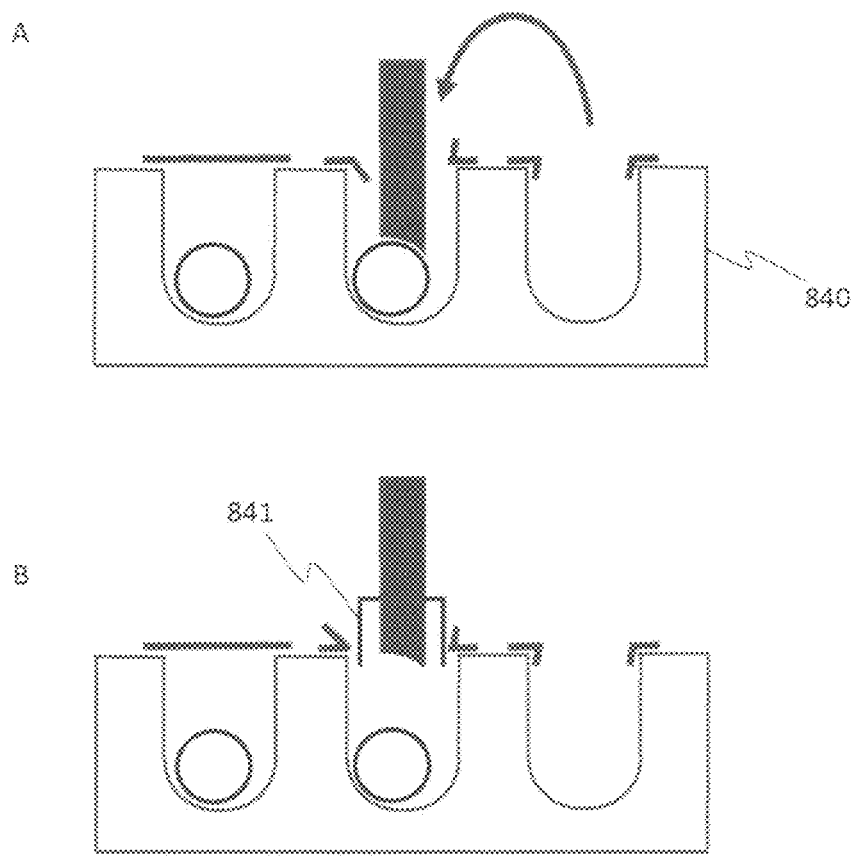

FIG. 12 shows a conceptual diagram of a mechanism that can be used when the cell disruption step of the present invention is automated. A plurality of containers 840 are integrally formed. A rolling body is preliminary sealed in each of the containers. In order to tear off the seal, a means by which a rotary shaft is directly pressed against the seal (FIG. 12A), a means by which an opening cutter 841 mounted on a rotary shaft is used for tearing (FIG. 12B) or the like can be used. The relative positions of the shaft and the container can automatically be changed and thus a plurality of samples can be disrupted one after another.

Figure 13:
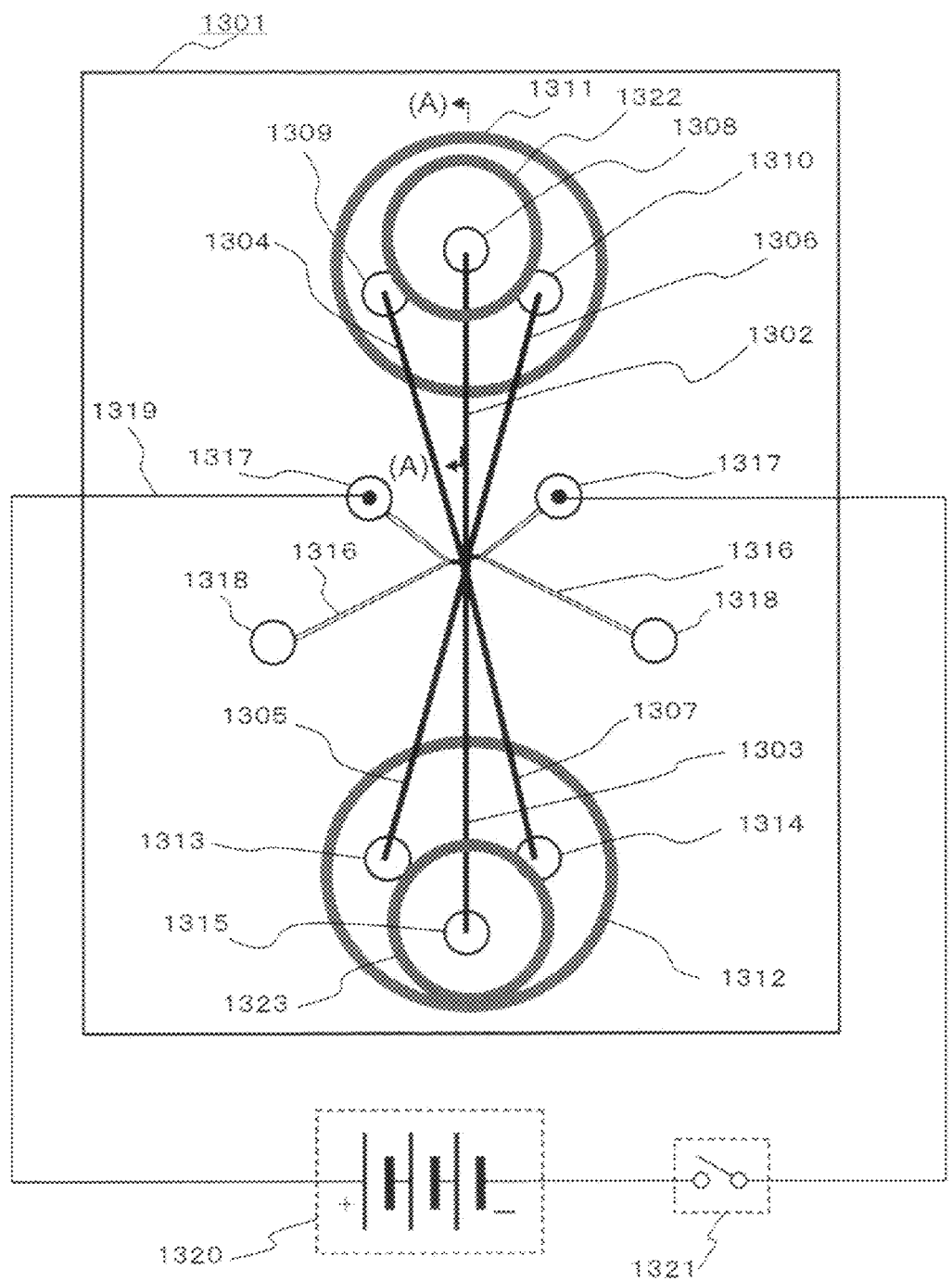

FIG. 13 shows an example of an on-chip cell sorter chip of the present invention that can be used in a system of devices for analyzing cells of the present invention. In a cell sorter chip 1301, three axially-symmetrical channels are symmetrically provided on the upstream side (1302, 1304, 1306) and the downstream side (1303, 1305, 1307) on a chip substrate. The three channels meet at a confluence of these three channels while maintaining the laminar flow and diverge into the three downstream channels while maintaining their states. Therefore, the upstream side 1302 of the middle channel for a sample to flow through extends to the downstream side 1303. For the other two side sheath flows, the upstream channel 1304 leads to the downstream side 1305 and the upstream channel 1306 leads to the downstream channel 1307. The inlets of the three upstream channels are linked with the inlet apertures 1308, 1309 and 1310, respectively. In particular, the inlet aperture 1308 provided at the upstream end of the channel for the sample to flow through and connected to a sample solution reservoir 1322 is typically (but without limitation) arranged such that it is isolated from the inlet apertures 1309 and 1310 for the channels for a sheath solution stored in a sheath solution reservoir 1311 to flow through, by providing a small ring-like cap (or a plug) so that the sample solution does not diffuse. The reservoir at the downstream side is similarly arranged as the upstream side, where a waste fluid reservoir 1312 is linked with outlet apertures 1313 and 1314 for the channels for two side sheath solutions to flow through, whereas a reservoir 1323 for collecting a purified sample is linked with an outlet aperture 1315 for a collected/purified sample. The outlet aperture 1315 is typically (but without limitation) provided with a small ring-like cap so that the collected purified sample does not diffuse to the waste fluid reservoir.

Moreover, if a flow velocity is generated by a gravity-type means that utilizes the difference in the heights between the liquid levels of the sample and sheath solution reservoirs and the liquid levels of the waste fluid and collected fluid reservoirs, or a flow velocity is generated by applying a cap on the upper surface of the reservoir to give pressure to the liquid level using pressurized air, then the shape of cross-sections of the channels and the distance from the confluence to the solution inlets are preferably identical so that the speeds of the three flows are the same for the three channels extending upstream and downstream from the confluence, since an ideal laminar flow can be generated at the confluence. The ratio of the cross-section of the inside sample/collected sample reservoir to the cross-section of the side sheath flow (or the waste fluid) reservoir is preferably set to 1 (sample collecting reservoir): 2 (side sheath solution reservoir/waste fluid reservoir). This is because if the change in the liquid level in each reservoir differs from each other, then the decreasing rates of the liquid levels also differ from each other, eventually disturbing the generation of a laminar flow at the confluence. Therefore, since the flowing amounts of the liquids per unit time is 1:2 between the sample that has one inlet and the sheath solution that has two inlets, the ratio of the cross-sections of the reservoirs was set to 1:2 so that the liquid levels are identical. In general, the ratio of the net cross-sectional areas of the channels linked to the reservoirs preferably corresponds to the ratio of the cross-sectional areas of the reservoirs.

Next, electrodes are provided at the confluence where there is no wall and the three laminar flows and all of the six channels meet. The electrodes are typically gel electrodes. The gel, for example, is an agarose gel containing NaCl so that the electrolyte can serve as the current carrier. To allow the leading end of the gel to directly make contact with the channel, the agarose gel in a sol state is introduced into a Y-shaped gel-filling channel 1316 from an inlet 1317 which can travel toward an outlet 1318 so that the gel does not enter the channels of the cell sorter and thus stops at the border line by the surface tension. An advantage of using a gel electrode is that by inserting an electric wire 1319 such as a platinum wire that is connected to a power source 1320 for applying an electric field into this gel introduction point, current can be produced without causing a bubble at the boundary between the channel and the gel electrode even when the voltage is increased to a voltage that would cause a bubble in the channel with a general metal electrode. On and off of the electric field application can be controlled, for example, by a switch 1321.

Figure 14:
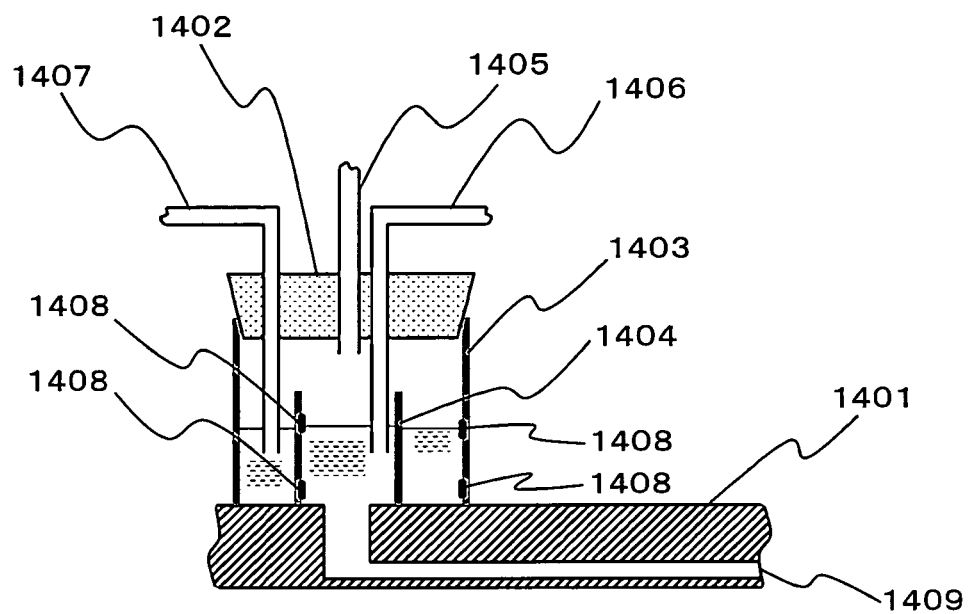
FIG. 14 A figure schematically showing an exemplary chip configuration of a sample reservoir region of the cell sorter module according to the present invention.

FIG. 14 schematically shows an exemplary cross-section of the upstream reservoir, particularly taken at line A-A in FIG. 13. A cell sorter chip 1401 is embedded with a channel 1409. In a typical embodiment, covering of the upper surface of the outer sheath solution reservoir 1403 by a cap 1402 makes it possible to supply pressurized air from a pressurized air introducing pipe 1405 thereby giving an appropriate flow velocity. As can be appreciated from the figure, the channel 1409 for a sample to flow through is linked to a sample reservoir 1404 such that the sample solution and the sheath solution do not mix with each other. In a preferable and typical embodiment, the cross-section ratio between the sample reservoir and the sheath solution reservoir is set to 1:2 since the ratio of the number of channels is 1:2, thereby adjusting the liquid levels of the reservoirs linking to the channels to be the same.

In order to process a larger amount of sample, a mechanism for supplying a liquid can be added. This mechanism incorporates a sample solution-introducing tube 1406 or a sheath solution-introducing tube 1407, and water level-measuring sensors 1408 utilizing conductive measurement on the wall surfaces of the reservoirs. By doing so, whenever the water level becomes lower than a certain level, a sample solution can be supplied through a tube to the certain level. The water level-measuring sensor 1408 may include electrodes, electrode pairs or the like that are disposed at the lower limit and the upper limit of the water level desired.

Figure 15:
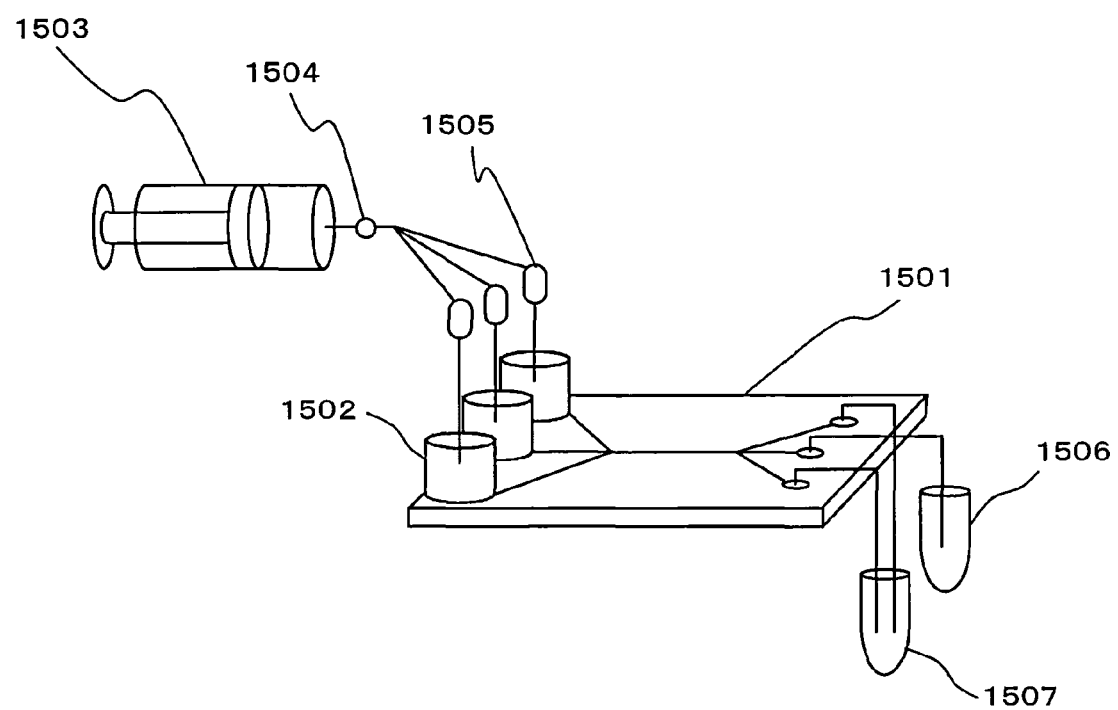
FIG. 15 A figure schematically showing an exemplary configuration of the image-detection-type single-cell separation/purification (cell sorter) module.

FIG. 15 shows another exemplary configuration for handling a large amount of sample in a cell sorter of the present invention. Three large-size reservoirs 1502 are disposed upstream of three respective channels on a chip 1501. They can be used to distribute pressure from an air pressure application device 1503 though a pressure sensor 1504 in a more flexible manner by a distribution valve 1505. In order to collect a sample, a sorted (purified) sample and a waste fluid are both collected into a sorted sample collecting reservoir 1506 and a waste fluid collecting reservoir 1507, respectively, that are disposed at a position lower than the chip.

Figure 16:
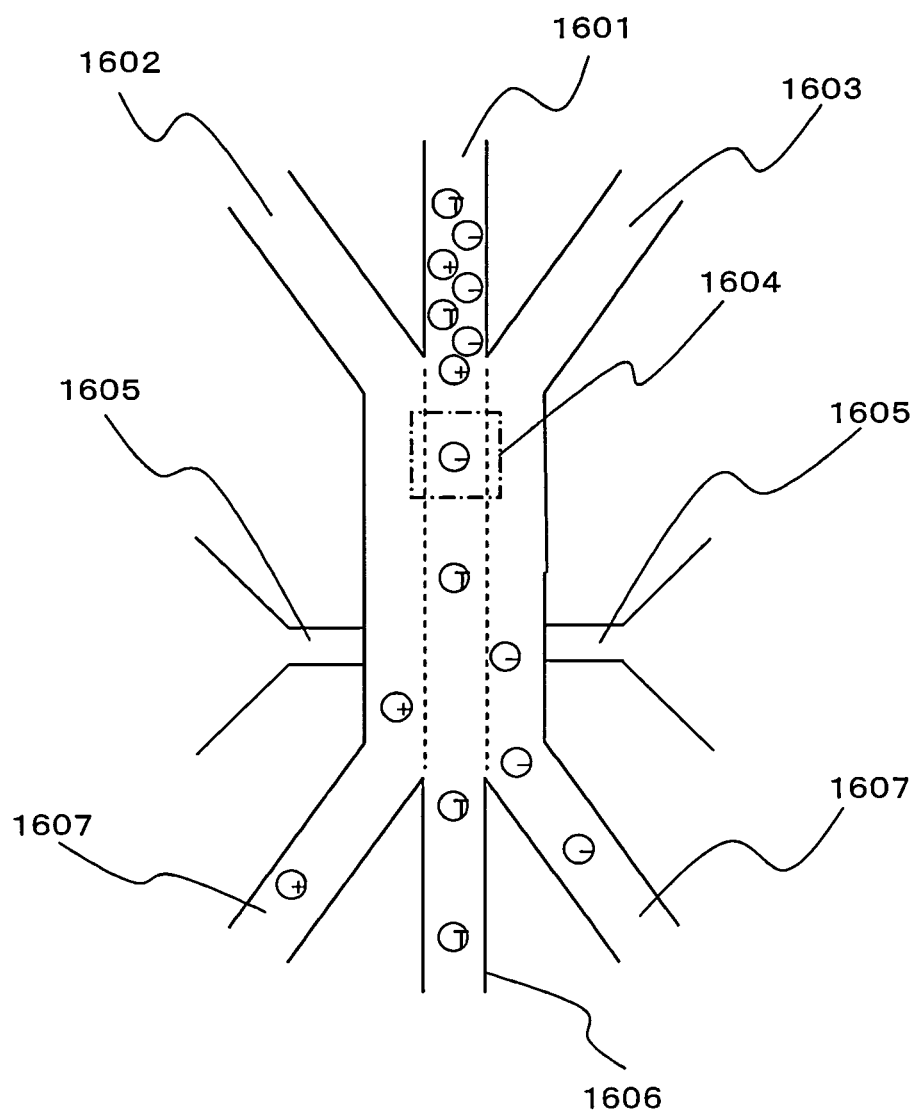
FIG. 16 A figure schematically showing an example of the process for purifying a cell in the image-detection-type single-cell separation/purification (cell sorter) module in FIG. 15.

FIG. 16 schematically shows an actual procedure for collecting a sample into a chip. A sample solution flow 1601 running from the upstream side is sandwiched between two side sheath solution flows 1602 and 1603 and proceeds to a cell monitoring region 1604 while maintaining the alignment of the flow. There, the shape of each cell, the presence or absence of a fluorescence label and the like are determined. Based on the result, cell separation is carried out on the downstream side. When a cell to be collected comes along, the cell is allowed to flow directly to a sorted sample collecting channel 1606 at the downstream side. When a cell or a microparticle to be discarded comes along, a voltage is applied to the two opposing gel electrodes 1605 so that it travels to either one of the two side sheath flows 1607 to be discarded regardless of whether its charge is positive or negative.

FIG. 17 is a schematic view for illustrating one of indicators for collecting cells in an image-processing-type cell sorter. In general, a cell is in the G0 cycle where a nucleus is present (FIG. 17A(a)), which is clearly recognized in an image as a black dot in the cell (FIG. 17B(a)). On the other hand, since a cell in the mitotic period has no nucleus (FIG. 17A(b)), no nucleus can be confirmed upon image recognition of the cell (FIG. 17B(b)). By a conventional labeling technique such as antibody labeling, it is difficult to confirm the state of a cell. According to the present invention, by way of such image recognition, collection of a cell undergoing mitosis according to the presence or absence of a nucleus in the cell, in addition to evaluation of the shape of the cell, becomes possible. Generally, most of the normal cells flowing in the blood are already terminally differentiated. However, according to the present invention, collection of cells having division capacity such as cancer cells or stem cells in the blood becomes possible by collecting cells undergoing mitosis in blood.

FIG. 18 shows an example of a timing diagram for actually operating the image-recognizing-type cell sorter of the present invention using a flashlight source. When a high-speed camera is used to observe cells traveling in a chip, in order to prevent blurring, spatial resolution of the camera per pixel is calculated based on the magnification of the objective lens. When a migration speed for the flow of the sample is defined, the traveling distance per pixel with the flow velocity is calculated so that the flashlight is turned on only during the time that takes for that traveling distance. Specifically, flashlight can be emitted once in every shutter interval following the expression below:

Flashing time=Pixel size/Flow velocity

For example, a pixel size of a camera with a shutter speed of ½,₀₀₀ second is 12 so that the flashlight is turned 20× objective lens is used for observation, the pixel resolution is 0.6 μr example, a pixel size of a camer 60 cm/s, an image without blurring can actually be captured by an LED light source capable of flashing at a speed of 1 d of

INDUSTRIAL APPLICABILITY

The present invention is useful for purifying a minute amount of target cells in the blood for each single cell, and accurately analyzing gene information and expression information of that target cell. The present invention is useful for purifying a minute amount of target cells having spores, such as anthrax, at a single cell level, and accurately and rapidly analyzing gene information and expression information of the target cells.

REFERENCE NUMERALS

1 System of devices for analyzing cells
10 Cell concentration/staining/decoloring module
101 Cell sample container
102 Stain agent container
103 Wash agent container
104 Dispensing head
105 Turntable
106 Concentrating/decoloring filter
107 Concentrating chamber
108 Chamber
109 Pressure pump
110 Waste fluid collecting tube
111 Collecting head
112 Collecting tube
113 Collecting chip
114 Chassis
20 Image-detection-type 1 cell separation/purification module
201 Laser
202 Mirror
203 Condenser lens
204 Dichroic mirror
205 Filter
206 Photomultiplier for fluorescence detection
207 High-speed camera
208 Photodiode for forward-scattered light detection
209 Cell sorter chip
210 Chip substrate
211 Micro flow-path
212 Flow inlet
213 Flow outlet
214 Concentrated cell solution inlet
215 Cell concentration unit
216 Converging section
217 Sorting unit
218 Cell detection region
219 Flow of cells after application
220 Flow of particles before application
221 Flow outlet
222 Flow outlet
223 Waste fluid collection unit
224 Cell collection unit
225 V-shaped comb-like electrode
30 Single cell genomic analysis/expression analysis module
31 First temperature control unit
32 Second temperature control unit
301 Reaction vessel
302 Heat exchange vessel
303 Liquid reservoir tank
304 Pump
305 Switching valve
306 Auxiliary temperature control mechanism
307 Inlet A
308 Inlet B
309 Outlet A
310 Outlet B
311 Sample solution
312 Fluorescence detector
313 Control/analysis unit
314 Check valve
315 Control signal
40 Transport module
401 Dispensing head
402 Dispensing chip
403 Z-axis travel guide
404 Z-axis travel motor
405 a, b-arm rotary motor
406 Chassis
50 Control/analysis module (computer)
801 Container
802 Minute amount of sample
803 Rolling body
804 Rotary shaft
805 Sample
806 Abrasive
810 Rolling body
811 Container
812 Flexible structure
813 Rotary shaft
814 Tip part
815 Spring mechanism
820 Curved cut
821 Mortar-shape cut
822 Engagement structure
823 Hemisphere rolling body
824 Oval-shaped rolling body
825 projection-like rolling body
826 Bowl-shaped rolling body
830 Container
831 Rolling body
832 Abrasive
833 Sealed
834 Sample
835 Rotary shaft
836 Components
840 Integrated containers
841 Opening cutter
1301 Cell sorter chip
1302, 1304, 1306 Upstream channel
1303, 1305, 1307 Downstream channel
1308 Inlet aperture for sample solution
1309, 1310 Inlet aperture for sheath solution
1311 Sheath solution reservoir
1312 Waste fluid reservoir
1313, 1314 Outlet aperture for sheath solution
1315 Outlet aperture for purified sample solution
1316 Flow path for gel filling
1317 Inlet aperture for gel filling
1318 Outlet aperture for gel filling
1319 Electric wire
1320 Power source
1321 Switch
1322 sample solution reservoir
1323 Reservoir for collecting purified sample
1401 Cell sorter chip
1402 Cap
1403 Sheath solution reservoir
1404 Sample solution reservoir
1405 pressurized air introducing pipe
1406 Sample solution-introducing tube
1407 Sheath solution-introducing tube
1408 Water level-measuring sensor
1409 Flow path
1501 Cell sorter chip 1502 Large-size reservoir
1503 Air pressure application device
1504 Pressure sensor
1505 Distribution valve
1506 Sorted sample collecting reservoir
1507 Waste fluid collecting reservoir
1601 Flow of sample solution
1602, 1603 Side sheath flow
1604 Cell monitoring region
1605 Gel electrode
1606 Sorted sample collecting channel
1607 Side sheath flow

The invention claimed is:

1. A system of devices for analyzing cells comprising:
(A) a first device for concentrating, staining and washing a cell sample solution derived from a subject;
(B) a second device for concentrating, separating and purifying the stained cell in the sample solution derived from the first device;
(C) a third device for performing gene analysis and expression analysis on the purified cell in the cell sample solution derived from the second device;
(D) a fourth device for sequentially transporting the cell sample solution from the first to the second and then to the third devices; and
(E) a control/analysis unit for controlling the performance of each of the devices and analyzing the cell sample, wherein
(a) the first device comprises:
a chamber provided with a filter for concentrating, staining and washing the cell in the cell sample solution;
containers for holding each of the cell sample solution, a stain solution and a wash solution; and
a mechanism for sequentially introducing each of the solutions of each container into the chambers,
(b) the second device comprises:
a cell sorter chip comprising a channel through which the cell sample solution containing cells including a target cell flows, wherein the channel comprises a first channel for concentrating the cells and a second channel, branching from the first channel, for detecting the concentrated cells and sorting the target cell;
a mechanism that applies external force to the cells flowing through each of the channels such that the cells flowing through each of the channels are concentrated in the first channel and converged toward a desired direction in the second channel; and
an optical system comprising light irradiation means for irradiating the cells flowing through the second channel with light, and a high-speed camera that captures images of the cells at an image-capturing rate of at least 200 frames/second, and
(c) the third device comprises:
a reaction vessel to which the sample solution is added for reaction;
a heat exchange vessel that exchanges heat with the reaction vessel; and
a temperature control mechanism for controlling the temperature of the heat exchange vessel.

2. The system of devices for analyzing cells according to claim 1, further comprising a cell disruption mechanism upstream of the third device that performs gene analysis/expression analysis of the purified cells in the cell sample solution, wherein the disruption mechanism allows the content of the cells, which are transported by the fourth device that transports the cell sample solution, to elute from the cells into the sample solution by cell disruption, and
wherein the control/analysis unit controls each of the above members such that the cell sample solution from the second device is transported to the cell disruption mechanism by the fourth device that transports the cell sample solution, and the sample solution disrupted in the cell disruption mechanism is transported to the third device by the fourth device.

3. The system of devices for analyzing cells according to claim 2, wherein the cell disruption mechanism comprises:
a container for holding the cell sample; a disruption rolling body for disrupting the cells in the container; and an abrasive for disrupting the cells in the container, wherein the cell sample and the abrasive are added into the container, where the cell sample is disrupted by the action of the disruption rolling body whose revolving and orbital movements are strictly controlled.

4. The system of devices for analyzing cells according to claim 3, wherein the cell disruption mechanism further comprises a rotary shaft,
wherein the disruption rolling body rotates inside the container by being pressed from above by the rotary shaft, where the friction force and the degree of sliding between the disruption rolling body and the rotary shaft are controlled by the pressure between the disruption rolling body and the rotary shaft.

5. The system of devices for analyzing cells according to claim 4, wherein the cell disruption mechanism comprises a mechanism that is capable of generating force of pressing the disruption rolling body in a direction perpendicular to the lateral face of the container by displacing the rotation axis of the disruption rolling body and the rotation axis of the rotary shaft.

6. The system of devices for analyzing cells according to claim 4, wherein the cell disruption mechanism comprises a mechanism that is capable of lifting and taking away the disruption rolling body from the container by suction caused by magnetic force or electrostatic force of the rotary shaft or by difference in gas pressure.

7. The system of devices for analyzing cells according to claim 3, wherein the cell disruption mechanism is provided with a driving mechanism equipped with a plurality of containers, wherein the driving mechanism shifts the positions of the containers, allowing an automatic exchange of the containers so that contamination among different cell samples can be eliminated.

8. The system of devices for analyzing cells according to claim 3, wherein the cell disruption mechanism is provided with the disruption rolling body is placed inside an unused container and sealed airtight with an airtight seal so as to ensure that the container and the disruption rolling body are not contaminated during disruption of the cell samples.

* * * * *